United States Patent
Mangold et al.

(10) Patent No.: US 11,406,248 B2
(45) Date of Patent: Aug. 9, 2022

(54) OPTICAL FIBER ARTICLE, ITS PRODUCTION AND USE

(71) Applicant: SCHOTT AG, Mainz (DE)

(72) Inventors: Stephanie Mangold, Schornsheim (DE); Thomas Weingärtner, Gau-Algesheim (DE); Oliver Fratzer, Egelsbach (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 17/038,486

(22) Filed: Sep. 30, 2020

(65) Prior Publication Data

US 2021/0093158 A1 Apr. 1, 2021

(30) Foreign Application Priority Data

Sep. 30, 2019 (DE) .................. 10 2019 126 259.3
Aug. 17, 2020 (EP) ..................... 20191378

(51) Int. Cl.
G02B 6/02 (2006.01)
A61B 1/00 (2006.01)
G02B 23/26 (2006.01)

(52) U.S. Cl.
CPC ........ *A61B 1/0017* (2013.01); *A61B 1/00167* (2013.01); *G02B 6/02033* (2013.01); *G02B 23/26* (2013.01)

(58) Field of Classification Search
None
See application file for complete search history.

(56) References Cited

U.S. PATENT DOCUMENTS

| | | | |
|---|---|---|---|
| 3,772,870 A | 11/1973 | Wong et al. | |
| 5,461,691 A | 10/1995 | Blum et al. | |
| 6,577,802 B1 * | 6/2003 | Chien | C03C 25/1065 385/128 |
| 2003/0045600 A1 * | 3/2003 | Fewkes | C03C 25/1065 522/172 |
| 2008/0050529 A1 | 2/2008 | Besson et al. | |
| 2014/0288247 A1 | 9/2014 | Burckhardt et al. | |

FOREIGN PATENT DOCUMENTS

| | | |
|---|---|---|
| CN | 104473718 | 4/2015 |
| DE | 2227213 | 12/1972 |
| EP | 3081544 | 10/2016 |
| EP | 2776490 | 2/2018 |
| WO | 93/11080 | 6/1993 |

(Continued)

OTHER PUBLICATIONS

Silane Coupling Agent KH-550, URL: https://www.chennbk.com/en/chem/Silane/020Coupling%20Agent%20KH-550, 2015, ChemBK.com.

(Continued)

*Primary Examiner* — Chad H Smith
(74) *Attorney, Agent, or Firm* — Ohlandt, Greeley, Ruggiero & Perle, L.L.P.

(57) ABSTRACT

The present disclosure relates to an optical fiber article and a method for the production of the optical fiber article. The present disclosure in particular relates to the use of the optical fiber article in a fiber bundle as light guide and/or image guide, for example in an endoscope.

20 Claims, 6 Drawing Sheets

(56) References Cited

FOREIGN PATENT DOCUMENTS

WO      0149625      7/2001
WO      02/06176      1/2002

OTHER PUBLICATIONS

Pasternack, R.M. et al., Attachment of 3-(Aminoprapyl) triethoxysilane on Silicon Oxide Surfaces: Dependence on Solution Temperature, Langmuir 2008, vol. 24, No. 22, pp. 12963-12971.
German Office Action dated May 7, 2020 from German Application No. 10 2019 126 259.3, 12 pages.
3-Aminopropyltriethoxysilane(919-30-2) IR1, URL: https://www.chemicalbook.com/SpectrumEN 919-30-2 1R1.htm; retrieved Apr. 28, 2020.

* cited by examiner

OPTICAL FIBER ARTICLE, ITS PRODUCTION AND USE

CROSS-REFERENCE TO RELATED APPLICATIONS

The present application claims the benefit of German Patent Application No. 10 2019 126 259.3, filed on Sep. 30, 2019, and European Patent Application No. 20191378.7, filed on Aug. 17, 2020, each of which is incorporated herein by reference.

BACKGROUND OF THE DISCLOSURE

1. Field of the Disclosure

The present disclosure relates to an optical fiber article and a method for the production of the optical fiber article. The present disclosure also relates to the use of the optical fiber article in a fiber bundle as light guide and/or image guide, for example in an endoscope.

2. Background of the Related Art

Optical fiber articles, such as for example glass fiber articles, may transmit light and/or data as light guides and/or image guides. Optical fiber articles are often used in the medical field, for example for therapeutic and/or diagnostic methods. Light guides and/or image guides are, for example, used for the flexible transport of light in measuring devices, microscopes, spectroscopes, inspection cameras and endoscopes. Very frequently, medical apparatuses such as endoscopes are autoclaved and/or sterilized. In the case of steam sterilization, the materials are subjected to high pressures, temperatures and high air moisture at the same time. Therefore, it is necessary that light guides and/or images guides for the use in medical apparatuses such as for example an endoscope are characterized by good autoclavability and/or sterilizability and high corrosion resistance so that they can be used for a long time. Therefore, optical fiber articles are required which increase the durability of medical apparatuses and result in reduced occurrence of corrosion. Furthermore, optical fiber articles having high temperature resistance and air humidity resistance would be desirable. At the same time, the optical fiber article should be characterized by a high bendability and good mechanical stability, in particular for use in endoscopes.

Often, optical fibers are covered with sizes as protection layer. Normally, optical fibers are provided with polymerizable coating compositions which cure during UV radiation. Such coating compositions often contain acrylates, methacrylates and other polymerizable components. However, such polymerizable coating compositions are not harmless to health. Furthermore, such coatings contain photoinitiators having effects on human health that are considered more and more critical. The use of such photopolymerizable substances in medical apparatuses is critical in particular if they contact human organs. Therefore, optical fiber articles are desirable that can be produced without components which are questionable with respect to health. In particular, the toxicity of the materials should be as low as possible, or the materials should not be toxic at all and they should not be a source of danger for the patient. Therefore, the provision of optical fibers with improved biocompatibility and reduced toxicity would be desirable.

US 2003/0045600 A1 describes a sizing agent which may contain silanes such as for example polyalkoxysilanes and polyhalosilanes. The size of US 2003/0045600 A1 may also contain halides such as chlorine or fluorine. Furthermore, US 2003/0045600 A1 describes a sizing agent which may contain polyether urethane acrylate as main constituent.

WO 01/49625 A1 describes an optical fiber with a UV curable size which may contain photopolymerizable compounds such as for example caprolactone (meth)acrylate or 4-hydroxybutyl (meth)acrylate. Furthermore, the size of WO 01/49625 A1 may contain photoinitiators such as for example 1-hydroxycyclohexyl phenyl ketone or 2,2-dimethoxy-2-phenylacetophe none.

SUMMARY OF THE DISCLOSURE

Therefore, it is an object of the present disclosure to overcome the disadvantages of the prior art. In particular, it is an object to provide an improved optical fiber article for use in medical and diagnostic apparatuses such as endoscopes. The optical fiber article should in particular be characterized by a high corrosion resistance, including resistance during steam sterilization, a long service life, a good bending load capacity, as well as a particularly high biocompatibility and reduced toxicity.

These objects are addressed in the present disclosure. In particular, the present disclosure provides an optical fiber article, comprising at least one optical fiber and a functional layer arranged on the surface thereof. The optical fiber comprises a fiber core and may contain a cladding arranged on the fiber core.

The functional layer may comprise at least one functional silane having the following structural formula:

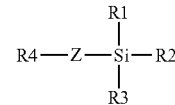

wherein Z is a branched or unbranched alkyl group or aryl group with 1 to 18 carbon atoms,
wherein R1, R2 and R3 are independently selected from hydrogen, oxygen, alkyl, hydroxyalkyl and hydroxyl, and wherein one, two or three of the groups R1, R2 or R3 is connected with the surface directly or indirectly via a covalent bond, and wherein R4 is selected from —NH$_2$, —NHR', —NR'R", glycidyloxy and —SH, wherein R' and R" are independently selected from alkyl, aminoalkyl, hydroxyalkyl and —(CH$_2$)$_m$NH$_2$, wherein m is 1 to 6.

In one aspect the present disclosure relates to an optical fiber article comprising at least one optical fiber and a functional layer which is arranged on the surface of the optical fiber, wherein the functional layer is characterized by the following absorption in an IR spectrum:
a. a ratio of the maximum absorption band height in the range of 800 cm$^{-1}$ to 1200 cm$^{-1}$ to the maximum absorption band height in the range of 1500 cm$^{-1}$ to 1900 cm$^{-1}$ is at least 2.0;
b. a ratio of the maximum absorption band height in the range of 2700 cm$^{-1}$ to 3000 cm$^{-1}$ to the maximum absorption band height in the range of 1500 cm$^{-1}$ to 1900 cm$^{-1}$ is at least 2.0; and
c. a ratio of the maximum absorption band height in the range of 800 cm$^{-1}$ to 1200 cm$^{-1}$ to the maximum absorption band height in the range of 2700 cm$^{-1}$ to 3000 cm$^{-1}$ is at least 1.1 and at most 2.0.

The optical fiber article having such an IR spectrum is obtained, when measures are implemented which are described herein. In preferable embodiments, the functional layer is characterized by an IR spectrum which substantially corresponds to FIG. 2 or FIG. 3.

"Optical fiber" means a fiber which is capable of transporting light over short or long distances. Such an optical fiber may, for example, be a glass fiber. The optical fiber comprises a core layer (also "fiber core"), a cladding layer (also short "cladding") and a functional layer which is arranged on the surface of the cladding layer.

"Optical fiber bundle" means a plurality of optical fibers. For example, an optical fiber bundle may consist of 10 or more optical fibers.

"Optical fiber article" means an article which comprises at least one optical fiber. It is also possible that the optical fiber article comprises a plurality of optical fibers. Optical fibers and optical fiber articles may, for example, be used in light guides and/or image guides. For the use in such light guides and/or image guides, for example, several optical fiber articles can be bonded to one another and can be embedded together in a sheath.

"Functional layer" means a layer which is arranged on the surface of the cladding layer and which at least partially, in particular substantially completely, covers the optical fiber. Inter alia, the functional layer is a layer which protects the optical fiber, for example from fractures (breaks). The functional layer may, for example, be formed from a size.

"Size" or "sizing agent" means a composition which serves for applying the functional layer onto optical fibers. After the production of the fiber the size can be applied e.g. by dipping, spraying or in a roll-to-roll method.

"Functional silane" means a silane compound which comprises at least one functional group which can undergo chemical reactions. Such a functional group may, for example, be an amino group. The functional silane may, for example, serve as a bonding agent and may function as a bridge between the surface of the cladding layer and an adhesive.

"Cladding layer" means a layer which is arranged below the functional layer and which surrounds a core layer. The cladding layer may, for example, contain glass or a polymer such as for example polyimide. In particular, the cladding layer contributes to the light transport function of the optical fiber.

"Core layer" means the inner layer of the optical fiber, and it may be surrounded by the cladding layer. The core layer may, for example, contain glass or a polymer such as for example polycarbonate. In particular, the core layer together with the cladding layer contributes to the light transport function of the optical fiber.

DETAILED DESCRIPTION OF THE DISCLOSURE

In the following detailed description measures and features are mentioned which may make a contribution to the success according to the present disclosure. It is not required to implement all measures in one optical fiber article. Rather, it is possible to achieve intended improvements, when only some of the following measures are implemented.

In an embodiment, the functional layer comprises a functional silane. The functional silane comprises free functional groups, such as for example amino groups, which have not reacted with acrylates or other reactive compounds. The functional silane mediates good adhesion of the functional layer to the surface of the cladding layer. A good adhesion of the functional layer to the optical fiber results in a protective effect of the functional layer, such as for example in the protection from microcracks and fractures, in particular in the case of repeated and increased bending load of the fiber article. In addition, the functional silane imparts good bonding characteristics to the functional layer at the side facing away from the optical fiber. Hence, the functional layer is capable of providing good adhesion with further material, such as for example an adhesive. With the functional silane a good bonding ability of the optical fiber article is achieved. When, for example, several optical fiber articles are embedded in a sheath and bonded, a better adhesion of the optical fiber articles is achieved, both, among each other and to the sheath. Such a sheath may, for example, contain stainless steel or plastic material.

Preferably, the alkyl group in Z comprises at least one carbon atom, at least 2 carbon atoms, at least 3 carbon atoms or at least 4 carbon atoms. Preferably, the alkyl group in Z comprises at most 25 carbon atoms, further preferably at most 20 carbon atoms, further preferably at most 15 carbon atoms, further preferably at most 12 carbon atoms, further preferably at most 10 carbon atoms, further preferably at most 9 carbon atoms, further preferably at most 8 carbon atoms, further preferably at most 7 carbon atoms. In embodiments, the alkyl group in Z comprises 1 to 25 carbon atoms, further preferably 1 to 20 carbon atoms, further preferably 2 to 15 carbon atoms or 3 to 12 carbon atoms. In preferable embodiments, the alkyl group in Z comprises 3 to 8 carbon atoms. The number of carbon atoms influences the sliding properties of the optical fibers. Thus, the optical fibers and/or the optical fiber article can be bent more often and to a stronger extent without fracturing. Improved sliding properties also result in the fact that the optical fibers slide well against each other and at the same time do not bond to one another. Preferably, the alkyl group in Z is an unbranched alkyl group.

Figure 1:
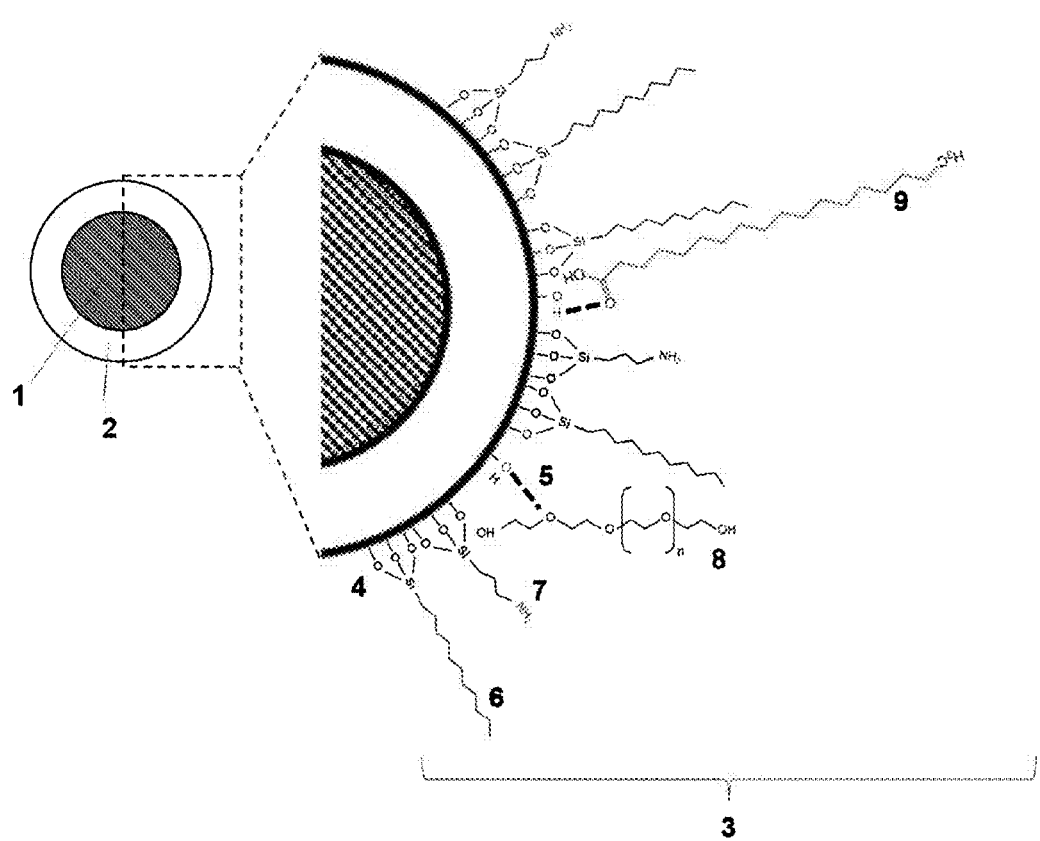
FIG. 1 is a schematic representation of an optical glass fiber with a fiber core (1) and a cladding (2). The functional layer (3) is connected with the surface of the cladding layer via covalent siloxane bonds (4) and non-covalent hydrogen bonds (5). The functional layer comprises, for example, an alkylsilane (6), an aminosilane (7), a polyethylene glycol (8) and a fatty acid (9).

The groups R1, R2 and R3 may independently be selected from hydrogen, oxygen, alkyl, alkyloxy, hydroxyalkyl and hydroxyl, wherein one, two or three of the groups R1, R2 or R3 are connected with the surface of the optical fiber directly or indirectly via a covalent bond. In other words, for example, one of the groups R1, R2 or R3 can be an alkyl group (e.g. methyl group) or an alkyloxy group (e.g. methoxy or ethoxy group), and two further groups are oxygen and are bound to the surface of the fiber via a siloxane group (cf. FIG. 1). The alkyl part of R1, R2 and/or R3 may have a chain length of 1 to 6, in particular 1 to 3 carbon atoms. In particular, one, two or three of the groups R1, R2 or R3 of the functional silane are connected with the surface of the fiber directly or indirectly via a covalent bond. Preferably, one, two or three of the groups R1, R2 and R3 is an (—X—R''') group, wherein X is selected from oxygen, selenium and sulfur and wherein R''' is selected from an alkyl group, hydrogen and the surface of the fiber. Further preferably, one, two or three of the groups R1, R2 and R3 is an (—X—R''') group, wherein X is oxygen and wherein R''' is selected from an alkyl group, hydrogen and the surface of the fiber. Further preferably, one, two or three of the groups R1, R2 and R3 is an (—X—R''') group, wherein X is oxygen and wherein R''' is the surface of the fiber. Further preferably, two or three of the groups R1, R2 and R3 are a (—X—R''') group, wherein X is oxygen and wherein R''' is the surface of the fiber. The alkyl group may have a carbon chain length in the range of 1 to 6, in particular of 1 to 3 carbon atoms. For example, the functional silane forms one or two or three siloxane connections with the surface of the cladding layer. So, the functional silane described here makes a substantial contribution to the adhesion of the functional layer to the optical fiber.

R4 may be selected from —NH$_2$, —NHR', —NR'R'', glycidyloxy and —SH, wherein R' and R'' are independently selected from alkyl, aminoalkyl, hydroxyalkyl and —(CH$_2$)$_m$NH$_2$, wherein m is 1 to 6, in particular 1 to 3. In embodiments, R4 is selected from —NH$_2$, —NHR', and —NR'R'', wherein R' and R'' are independently selected from alkyl, aminoalkyl, hydroxyalkyl and —(CH$_2$)$_m$NH$_2$, wherein m is 1 to 6, further preferably m is 1 to 5, further preferably 1 to 4, further preferably 1 to 3, further preferably 1 to 2. Preferably, R4 is selected from —NH$_2$ and —NHR', wherein R' is selected from alkyl, aminoalkyl, hydroxyalkyl and —(CH$_2$)$_m$NH$_2$, wherein m is 1 to 6, preferably m is 1 to 5, preferably 1 to 4, preferably 1 to 3, preferably 1 to 2. Preferably, R4 is selected from —NH$_2$ and —NHR', wherein R' is alkyl. In a preferable embodiment, R4 is —NH$_2$. In a preferable embodiment R4 is —(CH$_2$)$_2$NH$_2$. The functional silane with such a group R4 allows for good adhesion properties and bonding, for example when optical fiber articles are embedded with an adhesive in a sheath.

In a preferable embodiment, the functional silane has the following structural formula:

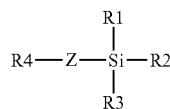

wherein R1, R2 and R3 are an (—X—R''') group, wherein X is oxygen and wherein R''' is the surface of the fiber; wherein Z is an unbranched alkyl group with 3 carbon atoms; and wherein R4 is selected from —NH$_2$ and —NHR', wherein R'' is —(CH$_2$)$_m$NH$_2$, wherein m=2.

In a preferable embodiment, the functional silane has the following structural formula:

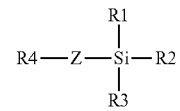

wherein R1, R2 and R3 are an (—X—R''') group; wherein X is oxygen and wherein R''' is the surface of the fiber; wherein R4 is —NH$_2$; and wherein Z is an unbranched alkyl group with 1 to 10 carbon atoms, preferably with 2 to 9 carbon atoms, preferably with 3 to 8 carbon atoms.

In another preferable embodiment, the functional silane has the following structural formula:

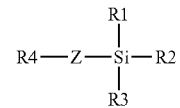

wherein R1, R2 and R3 are an (—X—R''') group, wherein X is oxygen and wherein R''' is the surface of the fiber; wherein R1, R2 and R3 are connected with the surface of the fiber directly via a covalent bond; wherein R4 is —NHR'; wherein R' is —(CH$_2$)$_m$NH$_2$, wherein m=2; and wherein Z is an unbranched alkyl group with 1 to 10 carbon atoms, preferably of 2 to 9 carbon atoms, preferably of 3 to 8 carbon atoms.

In a preferable embodiment, Z=3 and R4 is NH$_2$ or NHR', with R'=—(CH$_2$)$_m$NH$_2$ and m=2. Examples for functional silanes that may be used according to the present disclosure are N-[3-(trimethoxysilyl)propyl]ethylenediamine, N-[3-(triethoxysilyl)propyl]ethylenediamine, 3-aminopropyl diethoxy methyl silane, 3-glycidyloxypropyl triethoxy silane, 3-glycidoxypropyl dimethoxy methyl silane, 3-glycidoxypropyl diethoxy methyl silane and combinations thereof and/or their reaction products with the surface of the fiber, in particular their derivatives being connected with the surface of the fiber via one, two or three covalent bonds.

In certain embodiments, the functional layer comprises a plurality of functional silanes. In certain embodiments, the functional layer comprises at least two functional silanes, at least three functional silanes or at least four functional silanes.

Preferably, the functional layer comprises the functional silane in a proportion of at least 0.1% by weight, preferably of at least 0.5% by weight, preferably of at least 0.9% by weight, preferably of at least 1.2% by weight, preferably of at least 1.5% by weight, preferably of at least 1.8% by weight, preferably of at least 2% by weight. Preferably, the functional layer comprises the functional silane in a proportion of at most 70% by weight, preferably of at most 60% by weight, preferably of at most 50% by weight, preferably of at most 40% by weight, preferably of at most 30% by weight, preferably of at most 25% by weight, preferably of at most 15% by weight. In preferable embodiments, the functional layer comprises the functional silane in a proportion of 0.1 to 70% by weight, preferably of 0.5 to 50% by weight, preferably of 0.9 to 40% by weight, preferably of 1.2 to 30% by weight, preferably of 1.5 to 15% by weight. In particularly preferable embodiments, the functional layer comprises the functional silane in a proportion of 1 to 40% by weight, or of 2 to 15% by weight. If the proportion of functional silane is too low, adhesion of the functional layer to the surface of the cladding layer decreases, so that the optical fiber forms microcracks and fractures more easily. If the proportion of functional silane is too high, sliding of the optical fibers against each other is reduced, and they show a tendency to adhere to each other. In the case of repeated and increased bending loads, this results in an increased formation of microcracks and fractures. It has to be noted that in comparison to functional layers of the prior art the content of functional silane in said functional layer is relatively high, because the sizes which are used for the production of the functional layer preferably substantially do not contain polymerizable solvents, such as acrylates or methacrylates. The solvents used in the sizes do not remain in the functional layer after drying.

In embodiments, the functional layer comprises at least one alkylsilane as an alternative or in addition to the functional silane. Preferably, the functional layer comprises an alkylsilane covalently bound to the surface of the fiber. Preferably, the alkylsilane has the following structural formula:

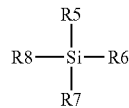

wherein R5, R6 and R7 are independently selected from hydrogen, oxygen, alkyl, alkyloxy, hydroxyalkyl and hydroxyl, and wherein one, two or three of the groups R5, R6 or R7 is connected with the surface of the fiber directly or indirectly via a covalent bond,
wherein R8 is selected from branched and unbranched alkyl group with 1 to 25 carbon atoms. The alkylsilane improves the hydrolytic resistance of the optical fiber and reduces the surface energy.

Preferably, the alkyl group in R8 of the alkylsilane comprises at least one carbon atom, at least 2 carbon atoms, at least 5 or at least 8 carbon atoms. Preferably, the alkyl group in R8 comprises at most 25 carbon atoms, preferably at most 20 carbon atoms, preferably at most 15 carbon atoms, preferably at least at most 12 carbon atoms, preferably at most 10 carbon atoms. In embodiments, the alkyl group in R8 comprises 1 to 25 carbon atoms, preferably 1 to 20 carbon atoms, preferably 1 to 15 carbon atoms, preferably 3 to 12 carbon atoms. In preferable embodiments, the alkyl group in R8 comprises 5 to 10 carbon atoms, or 8 to 15 carbon atoms. The chain length of the alkylsilane improves sliding of the optical fibers against each other, for example within an optical fiber bundle, and prevents or mitigates the bonding of the optical fibers among each other. This results in an improved handleability and the ability of the fibers in the bundle to be separated into single fibers. Preferably, the alkyl group in R8 of the alkylsilane is an unbranched alkyl group. Preferably, one, two or three of the groups R5, R6 and R7 is an (—X—R''') group, wherein X is selected from oxygen, selenium and sulfur, and wherein R''' is selected from an alkyl group, hydrogen and the surface of the fiber. Further preferably, one, two or three of the groups R5, R6 and R7 is an (—X—R''') group, wherein X is oxygen, and wherein R''' is selected from an alkyl group, hydrogen and the surface of the fiber. Further preferably, one, two or three of the groups R5, R6 and R7 is an (—X—R''') group, wherein X is oxygen, and wherein R''' is the surface of the fiber. Further preferably, two or three of the groups R5, R6 and R7 are a (—X—R''') group, wherein X is oxygen and wherein R''' is the surface of the fiber. For example, the alkylsilane forms one or two or three siloxane connections with an Si—OH group of the surface of the fiber. The alkylsilane described here improves the adhesion of the functional layer to the surface of the fiber. Furthermore, the alkylsilane described here improves the pliability of the optical fibers, for example in an optical fiber bundle, and reduces the mutual friction of the optical fibers.

Preferably, the alkylsilane has the following structural formula:

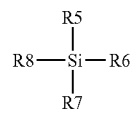

wherein R5, R6 and R7 are an (—X—R''') group; wherein X is oxygen and wherein R''' is the surface of the fiber; wherein R5, R6 and R7 are connected with the surface of the fiber directly via a covalent bond; and wherein R8 is an unbranched alkyl group with 1 to 15 carbon atoms, preferably with 1 to 12 carbon atoms, preferably of 1 to 10 carbon atoms, preferably with 1 to 9 carbon atoms, preferably with 3 to 8 or exactly 8 carbon atoms.

Examples of alkylsilanes which may be used according to the present disclosure are trimethoxy propyl silane, trimethoxy octyl silane, triethoxy octyl silane, trimethoxy decyl silane, triethoxy decyl silane, trimethoxy dodecyl silane, triethoxy dodecyl silane, trimethoxy methyl silane, n-propyl triethoxy silane, triethoxy methyl silane, dimethoxy dimethyl silane, diethoxy dimethyl silane, and/or their reaction products with the surface of the fiber, in particular their derivatives being connected with the surface of the fiber via one, two or three covalent bonds.

In certain embodiments, the functional layer comprises a plurality of alkylsilanes. In certain embodiments, the functional layer comprises at least two alkylsilanes, at least three alkylsilanes or at least four alkylsilanes.

Preferably, the functional layer comprises the alkylsilane in a proportion of at least 0.8% by weight, preferably of at least 1% by weight, preferably of at least 2% by weight, preferably of at least 3% by weight, preferably of at least 4% by weight, preferably of at least 5% by weight, preferably of at least 6% by weight. Preferably, the functional layer comprises at least one alkylsilane in a proportion of at most 65% by weight, preferably of at most 60% by weight, preferably of at most 55% by weight, preferably of at most 50% by weight, preferably of at most 45% by weight, preferably of at most 40% by weight, preferably of at most 35% by weight. In preferable embodiments, the functional layer comprises the alkylsilane in a proportion of 0.8 to 65% by weight, preferably of 1 to 60% by weight, preferably of 29 to 55% by weight, preferably of 3 to 50% by weight, preferably of 4 to 45% by weight. In particularly preferable embodiments, the functional layer comprises the alkylsilane in a proportion of 6 to 35% by weight. If the proportion of alkylsilane is too low, the optical fibers' pliability and chemical resistance may be reduced, which may result in an increased friction between the optical fibers, for example in an optical fiber bundle. Hence, microcracks and fractures may form more quickly. Furthermore, too low a proportion of alkylsilane reduces the chemical stability of the optical fiber, for example with respect to acids. If the proportion of alkylsilane is too high, cohesion of the optical fibers among each other, for example in an optical fiber bundle, may be reduced.

In embodiments, the functional layer, comprises a polyethylene glycol (PEG) silane as an alternative or in addition to the functional silane and/or the alkylsilane. Preferably, the functional layer comprises a PEG silane covalently bound to the surface of the fiber. Preferably, the PEG silane has the following structural formula:

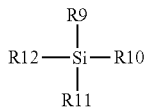

wherein R9, R10 and R11 are independently selected from hydrogen, oxygen, alkyl, alkyloxy, hydroxyalkyl and hydroxyl, and wherein one, two or three of the groups R9, R10 and R11 is connected with the surface of the fiber directly or indirectly via a covalent bond, and
wherein R12 comprises a polyethylene glycol group or consists thereof or is a derivative thereof, with a chain length of 5 to 900 ethylene oxide units. The PEG silane improves the hydrolytic stability of the optical fiber.

Preferably, the polyethylene glycol group or derivative thereof in R12 has a chain length of at least 3, preferably of at least 4, preferably of at least 5, preferably of at least 6, preferably of at least 7, preferably of at least 8 ethylene oxide units. Preferably, the polyethylene glycol group or derivative thereof has a chain length of at most 30, preferably of at most 25, preferably of at most 20, preferably of at most 15, preferably of at most 12 ethylene oxide units. In embodiments, the polyethylene glycol group has a chain length of 3 to 30, preferably of 4 to 25, preferably of 5 to 20 ethylene oxide units. In preferable embodiments, the polyethylene glycol group has a chain length of 8 to 12 ethylene oxide units. The chain length of the polyethylene glycol group or the derivative thereof improves cohesion of the optical fibers, for example in an optical fiber bundle, without bonding them to one another. Hence, pliability of the optical fibers, for example in an optical fiber bundle, is improved. The polyethylene glycol group in R12 may have a terminal group at its free end. The terminal group may be a hydroxyl or alkyloxy group, in particular a methoxy group.

Preferably, one, two or three of the groups R9, R10 and R11 is an (—X—R''') group, wherein X is selected from oxygen, selenium and sulfur and wherein R' is selected from an alkyl group, hydrogen and the surface of the fiber. Further preferably, one, two or three of the groups R9, R10 and R11 is an (—X—R''') group, wherein X is oxygen and wherein R' is selected from an alkyl group, hydrogen and the surface of the fiber. Further preferably, one, two or three of the groups R9, R10 and R11 is an (—X—R''') group, wherein X is oxygen and wherein R''' is the surface of the fiber. Further preferably, two or three of the groups R9, R10 and R11 are a (—X—R''') group, wherein X is oxygen and wherein R''' is the surface of the fiber. For example, the PEG silane forms one or two or three siloxane connections with a silicon group of the surface of the fiber. The PEG silane described improves adhesion of the functional layer to the surface of the fiber. Furthermore, the PEG silane described here improves pliability of the optical fibers, for example in an optical fiber bundle, and reduces the mutual friction of the optical fibers.

In preferable embodiments, the PEG silane has the following structural formula:

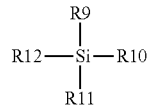

wherein R9, R10 and R11 are an (—X—R''') group; wherein X is oxygen and wherein R''' is the surface of the fiber; wherein R9, R10 and R11 are connected with the surface of the fiber directly via a covalent bond; and wherein R12 comprises a polyethylene glycol group, consists thereof or is a derivative thereof, with a chain length of 3 to 30, preferably of 4 to 25, preferably of 5 to 20, preferably of 8 to 12 ethylene oxide units.

Examples for PEG silanes which may be used according to the present invention are 2-[methoxy(polyethyleneoxy)$_{9-12}$propyl]trimethoxysilane, 2-[methoxy(polyethyleneoxy)$_{9-12}$propyl]triethoxysilane, 2-[ethoxy(polyethyleneoxy)$_{9-12}$propyl]triethoxysilane, [hydroxy(polyethyleneoxy)propyl]triethoxysilane, as well as their reaction products with the surface of the fiber, in particular their derivatives which are connected with the surface of the fiber via one, two or three covalent bonds.

In certain embodiments, the functional layer comprises a plurality of PEG silanes. In certain embodiments, the functional layer comprises at least two PEG silanes, at least three PEG silanes or at least four PEG silanes.

Preferably, the functional layer comprises at least one PEG silane in a proportion of at least 1% by weight, preferably of at least 5% by weight, preferably of at least 8% by weight, preferably of at least 11% by weight, preferably of at least 13% by weight, preferably of at least 15% by weight, preferably of at least 21% by weight. Preferably, the functional layer comprises at least one PEG silane in a proportion of at most 90% by weight, preferably of at most 85% by weight, preferably of at most 80% by weight, preferably of at most 75% by weight, preferably of at most 70% by weight, preferably of at most 65% by weight, preferably of at most 62% by weight. In preferable embodiments, the functional layer comprises the PEG silane in a proportion of 1 to 90% by weight, preferably of 5 to 85% by weight, preferably of 8 to 80% by weight, preferably of 11 to 75% by weight, preferably of 13 to 70% by weight. In a particularly preferable embodiment, the functional layer comprises the PEG silane in a proportion of 21 to 65% by weight. If the proportion of PEG silane is too low, this may result in a reduced cohesion of the optical fibers, for example in an optical fiber bundle. If the proportion of PEG silane is too high, this may result in a reduced cohesion of the optical fibers among each other, for example in an optical fiber bundle. Furthermore, too low a proportion of PEG silane may reduce chemical stability of the optical fiber. If the proportion of PEG silane is too high, the optical fibers may have a tendency to adhere to each other strongly, and the pliability is reduced. Hence, microcracks and fractures form more quickly.

In certain embodiments, the proportion by mass of the alkylsilane and/or PEG silane exceeds the proportion by mass of the functional silane. In certain embodiments, the proportion by mass of the alkylsilane and/or PEG silane exceeds the proportion by mass of the functional silane by a factor of at least 1.05, preferably at least 1.1, preferably at least 1.2, preferably at least 1.3, preferably at least 1.4, preferably at least 1.5, preferably at least 1.6. Preferably, the proportion by mass of the alkylsilane and/or PEG silane exceeds the proportion by mass of the functional silane by a factor of at most 100, at most 80, at most 60, preferably at most 40, preferably at most 30, preferably at most 20, or preferably at most 10.

In another embodiment, the proportion by mass of the functional silane exceeds the proportion by mass of the alkylsilane and/or PEG silane. In an embodiment, the proportion by mass of the functional silane exceeds the proportion by mass of the alkylsilane and/or PEG silane by a factor of at least 1.05, preferably at least 1.1, preferably at least 1.2, preferably at least 1.3, preferably at least 1.4, preferably at least 1.5, preferably at least 1.6. Preferably, the proportion by mass of the functional silane exceeds the proportion by mass of the alkylsilane and/or PEG silane by a factor of at most 100, at most 80, at most 60, preferably at most 40, preferably at most 30, preferably at most 20, or preferably at most 10.

In one embodiment, the functional layer comprises the following compounds:

| Compound | Proportion (% by weight) |
| --- | --- |
| functional silane | 0.1-70 |
| alkylsilane | 0.8-65 |
| PEG silane | — |

In one embodiment, the functional layer comprises the following compounds:

| Compound | Proportion (% by weight) |
| --- | --- |
| functional silane | 0.1-70 |
| alkylsilane | — |
| PEG silane | 1-90 |

In a further embodiment, the functional layer comprises the following compounds:

| Compound | Proportion (% by weight) |
| --- | --- |
| functional silane | 0.1-70 |
| alkylsilane | 0.8-65 |
| PEG silane | 1-90 |

In one embodiment, the functional layer comprises the following compounds:

| Compound | Proportion (% by weight) |
| --- | --- |
| functional silane | 2-40 |
| alkylsilane | 6-35 |
| PEG silane | — |

In one embodiment, the functional layer comprises the following compounds:

| Compound | Proportion (% by weight) |
| --- | --- |
| functional silane | 2-40 |
| alkylsilane | — |
| PEG silane | 21-65 |

In a further embodiment, the functional layer comprises the following compounds:

| Compound | Proportion (% by weight) |
| --- | --- |
| functional silane | 2-40 |
| alkylsilane | 6-35 |
| PEG silane | 21-65 |

Preferably, the functional layer, comprises at least one fatty acid as an alternative or in addition to at least one of the silanes. The fatty acid may be a saturated or an unsaturated fatty acid. In preferable embodiments, the fatty acid is a saturated fatty acid. The fatty acid increases the mechanical stability of the optical fiber and reduces the friction between the optical fibers. In addition, the fatty acid may form a hydrophobic protection layer around the fiber.

Preferably, the fatty acid has a chain length of at least 10 carbon atoms, preferably of at least 11, preferably of at least 12, preferably of at least 13, preferably of at least 14, preferably of at least 15, preferably of at least 16. Preferably, the fatty acid has a chain length of at most 40 carbon atoms, preferably of at most 35, preferably of at most 30, preferably of at most 28, preferably of at most 26, preferably of at most 24, preferably of at most 22. In embodiments, the fatty acid has a chain length of 10 to 40 carbon atoms, preferably of 11 to 35, preferably of 12 to 30, preferably of 13 to 28. In preferable embodiments, the fatty acid has a chain length of 14 to 22 carbon atoms. If the chain length is too low, adhesion of the functional layer to the surface of the cladding layer is reduced. If the chain length is too high, the optical fibers show a tendency to adhere to each other.

Preferably, the fatty acid has a melting point of at least 35° C., preferably of at least 39° C., preferably of at least 42° C., preferably of at least 48° C., preferably of at least 52° C., preferably of at least 54° C., preferably of at least 56° C., preferably of at least 58° C., preferably of at least 60° C., preferably of at least 65° C., preferably of at least 70° C. Preferably, the fatty acid has a melting point of at most 180° C., preferably of at most 160° C., preferably of at most 140° C., preferably of at most 120° C., preferably of at most 100° C., preferably of at most 95° C., preferably of at most 90° C. Preferably, the fatty acid has a melting point of 35° C. to 180° C., of 39° C. to 160° C., or of 42° C. to 100° C. In preferable embodiments, the fatty acid has a melting point of 53° C. to 90° C. If the melting point of the fatty aid is too low, this reduces adhesion of the functional layer to the optical fiber. This results in a reduced protection of the optical fiber, for example from microcracks and fractures. If the melting point of the fatty acid is too high, the optical fibers glue to each other too strongly. Hence, pliability is reduced, and in the case of increased and enhanced bending load it results in microcracks and fractures. Preferably, the fatty acid has a boiling point of at least 200° C., preferably of at least 220° C., preferably of at least 240° C., preferably of at least 260° C., preferably of at least 280° C., preferably of at least 300° C. Preferably, the fatty acid has a boiling point of at most 500° C., preferably of at most 400° C., preferably of at most 380° C., preferably of at most 330° C. Preferably, the fatty acid has a boiling point of 200° C. to 500° C., of 220° C. to 400° C., or of 240° C. to 380° C. Examples of fatty acids which can be used according to the present invention are capric acid, lauric acid, myristic acid, palmitic acid, margaric acid, stearic acid and arachidic acid.

In certain embodiments, the functional layer comprises a plurality of fatty acids. In certain embodiments, the functional layer comprises at least two fatty acids, at least three fatty acids or at least four fatty acids.

Preferably, the plurality of fatty acids has a melting point of its mixture of at least 35° C., preferably of at least 39° C., preferably of at least 42° C., preferably of at least 48° C., preferably of at least 52° C., preferably of at least 54° C., preferably of at least 56° C., preferably of at least 58° C., preferably of at least 60° C., preferably of at least 65° C., preferably of at least 70° C. Preferably, the plurality of fatty acids in the form of its mixture has a melting point of at most 180° C., preferably of at most 160° C., preferably of at most 140° C., preferably of at most 120° C., preferably of at most 100° C., preferably of at most 95° C., preferably of at most 90° C. Preferably, the plurality of fatty acids as mixture has a melting point of 35° C. to 180° C., of 39° C. to 160° C., or of 42° C. to 140° C. The melting point as mixture means the melting point of a mixture of the fatty acids which form the plurality of fatty acids in the used ratio. If the melting point of the plurality of fatty acids is too low, this results in reduced adhesion of the functional layer to the optical fiber. This in turn results in a reduced protection of the optical fiber, for example from microcracks and fractures. If the melting point of the plurality of fatty acids is too high, the optical fibers glue to each other too strongly. Hence, pliability is reduced, and in the case of increased and enhanced bending load it results in microcracks and fractures.

Preferably, the functional layer comprises one or more fatty acids in a proportion of at least 1% by weight, preferably of at least 2% by weight, preferably of at least 3% by weight, preferably of at least 4% by weight, preferably of at least 5% by weight, preferably of at least 6% by weight, preferably of at least 7% by weight. Preferably, the functional layer comprises at least one fatty acid in a proportion of at most 85% by weight, preferably of at most 80% by weight, preferably of at most 75% by weight, preferably of at most 70% by weight, preferably of at most 65% by weight, preferably of at most 60% by weight, preferably of at most 56% by weight. In preferable embodiments, the functional layer comprises at least one fatty acid in a proportion of 1-85% by weight, preferably of 2-80% by weight, preferably of 3-75% by weight, preferably of 4-70% by weight. In a preferable embodiment, the functional layer comprises one or more fatty acids in a total proportion of 7 to 56% by weight. If the proportion of the at least one fatty acid is too low, sliding of the optical fibers against each other is reduced. If the proportion of the at least one fatty acid is too high, the optical fibers bond to one another.

In one embodiment, the functional layer comprises the following compounds:

| Compound | Proportion (% by weight) |
| --- | --- |
| functional silane | 0.1-70 |
| alkylsilane | — |
| PEG silane | — |
| fatty acid | 1-85 |

In one embodiment, the functional layer comprises the following compounds:

| Compound | Proportion (% by weight) |
| --- | --- |
| functional silane | 2-40 |
| alkylsilane | — |
| PEG silane | — |
| fatty acid | 7-56 |

In one embodiment, the functional layer comprises the following compounds:

| Compound | Proportion (% by weight) |
| --- | --- |
| functional silane | 0.1-70 |
| alkylsilane | 0.8-65 |
| PEG silane | — |
| fatty acid | 1-85 |

In one embodiment, the functional layer comprises the following compounds:

| Compound | Proportion (% by weight) |
| --- | --- |
| functional silane | 2-40 |
| alkylsilane | 6-35 |
| PEG silane | — |
| fatty acid | 7-56 |

In one embodiment, the functional layer comprises the following compounds:

| Compound | Proportion (% by weight) |
| --- | --- |
| functional silane | 0.1-70 |
| alkylsilane | 0.8-65 |
| PEG silane | 1-90 |
| fatty acid | 1-85 |

In one embodiment, the functional layer comprises the following compounds:

| Compound | Proportion (% by weight) |
| --- | --- |
| functional silane | 2-40 |
| alkylsilane | 6-35 |
| PEG silane | 21-65 |
| fatty acid | 7-56 |

In embodiments, the functional layer comprises at least one polyvalent alcohol as an alternative or in addition to at least one of the silanes. Polyvalent alcohols according to the present invention may include glycerol, diethylene glycol or 1,5-pentanediol as well as alkane polyols, such as alkane diols and alkane triols, in particular alkane polyols having chain lengths of 2 to 10 carbon atoms, preferably of 3 to 8 carbon atoms. Preferably, the functional layer comprises at least one polyvalent alcohol in a proportion of at least 3% by weight, preferably of at least 5% by weight, preferably of at least 10% by weight, preferably of at least 15% by weight, preferably of at least 20% by weight, preferably of at least 25% by weight, preferably of at least 30% by weight. Preferably, the functional layer comprises at least one polyvalent alcohol in a proportion of at most 90% by weight, preferably of at most 87% by weight, preferably of at most 84% by weight, preferably of at most 81% by weight, preferably of at most 79% by weight, preferably of at most 77% by weight, preferably of at most 75% by weight. In preferable embodiments, the functional layer comprises the polyvalent alcohol in a proportion of 3 to 90% by weight, preferably of 5 to 87% by weight, preferably of 10 to 84% by weight, preferably of 15 to 81% by weight. In preferable embodiments, the functional layer comprises the polyvalent alcohol in a proportion of 30 to 75% by weight. The polyvalent alcohol improves sliding of optical fibers against each other and thus reduces occurrence of microcracks and fractures. The polyvalent alcohol improves handleability, the packing density and the fibers' ability to be separated from a bundle. The polyvalent alcohol may result in a desired "wet behavior", thus the property of a wet fiber article.

In an alternative or in addition to at least one of the silanes, the functional layer may comprise at least one polyalkylene oxide. Polyalkylene oxides according to the present disclosure may comprise polyglycols such as for example polyethylene glycol and polypropylene glycol as well as other polyalkylene oxides of monomers with 2 to 6 carbon atoms. Preferably, the functional layer comprises at least one polyalkylene oxide in a proportion of at least 2% by weight, preferably of at least 3% by weight, preferably of at least 4% by weight, preferably of at least 5% by weight, preferably of at least 6% by weight, preferably of at least 7% by weight, preferably of at least 8% by weight. Preferably, the functional layer comprises at least one polyalkylene oxide in a proportion of at most 90% by weight, preferably of at most 85% by weight, preferably of at most 80% by weight, preferably of at most 75% by weight, preferably of at most 70% by weight, preferably of at most 68% by weight, preferably of at most 65% by weight. In preferable embodiments, the functional layer comprises at least one polyalkylene oxide in a proportion of 1 to 90% by weight, preferably of 2 to 85% by weight, preferably of 3 to 80% by weight, preferably of 4 to 75% by weight. In a preferable embodiment, the functional layer comprises the polyalkylene oxide in a proportion of 8 to 65% by weight. The polyalkylene oxide reduces friction between the optical fibers and improves mechanical stability of the optical fibers. Furthermore, the polyalkylene oxide improves cohesion of optical fibers, for example in an optical fiber bundle.

In some embodiments, the polyalkylene oxide has a chain length of at least 3, preferably of at least 4, preferably of at least 5, preferably of at least 6, preferably of at least 7, preferably of at least 8 alkylene oxide units. Preferably, the polyalkylene oxide has a chain length of at most 100, preferably of at most 75, preferably of at most 50, preferably of at most 20, preferably of at most 14 alkylene oxide units. In embodiments, the polyalkylene oxide has a chain length of 3 to 100, preferably of 4 to 50, preferably of 6 to 20 alkylene oxide units. In preferable embodiments, the polyalkylene oxide has a chain length of 7 to 14 alkylene oxide units. It is advantageous to use polyalkylene oxides which at room temperature (20° C., 1013 hPa) are liquid.

In one embodiment, the functional layer comprises the following compounds:

| Compound | Proportion (% by weight) |
| --- | --- |
| functional silane | 0.1-70 |
| alkylsilane | 0.8-65 |
| PEG silane | — |
| fatty acid | — |
| polyvalent alcohol | — |
| polyalkylene oxide | –90 |

In one embodiment, the functional layer comprises the following compounds:

| Compound | Proportion (% by weight) |
| --- | --- |
| functional silane | 2-40 |
| alkylsilane | 6-35 |
| PEG silane | — |
| fatty acid | — |
| polyvalent alcohol | — |
| polyalkylene oxide | 8-65 |

In one embodiment, the functional layer comprises the following compounds:

| Compound | Proportion (% by weight) |
| --- | --- |
| functional silane | 0.1-70 |
| alkylsilane | 0.8-65 |
| PEG silane | — |
| fatty acid | 1-85 |
| polyvalent alcohol | — |
| polyalkylene oxide | –90 |

In one embodiment, the functional layer comprises the following compounds:

| Compound | Proportion (% by weight) |
| --- | --- |
| functional silane | 2-40 |
| alkylsilane | 6-35 |
| PEG silane | — |
| fatty acid | 7-56 |
| polyvalent alcohol | — |
| polyalkylene oxide | 8-65 |

In one embodiment, the functional layer comprises the following compounds:

| Compound | Proportion (% by weight) |
| --- | --- |
| functional silane | 0.1-70 |
| alkylsilane | 0.8-65 |
| PEG silane | 1-90 |
| fatty acid | 1-85 |
| polyvalent alcohol | 3-90 |
| polyalkylene oxide | –90 |

In one embodiment, the functional layer comprises the following compounds:

| Compound | Proportion (% by weight) |
| --- | --- |
| functional silane | 2-40 |
| alkylsilane | 6-35 |
| PEG silane | 21-65 |
| fatty acid | 7-56 |
| polyvalent alcohol | 30-75 |
| polyalkylene oxide | 8-65 |

In one embodiment, the functional layer comprises the following compounds:

| Compound | Proportion (% by weight) |
| --- | --- |
| functional silane | 0.1-70 |
| alkylsilane | 0.8-65 |
| PEG silane | 1-90 |

| Compound | Proportion (% by weight) |
| --- | --- |
| fatty acid | 1-85 |
| polyvalent alcohol | 3-90 |
| polyalkylene oxide | –90 |

In one embodiment, the functional layer comprises the following compounds:

| Compound | Proportion (% by weight) |
| --- | --- |
| functional silane | 2-40 |
| alkylsilane | 6-35 |
| PEG silane | 21-65 |
| fatty acid | 7-56 |
| polyvalent alcohol | 30-75 |
| polyalkylene oxide | 8-65 |

In one embodiment, the functional layer comprises the following compounds:

| Compound | Proportion (% by weight) |
| --- | --- |
| functional silane | 5-30 |
| alkylsilane | 12-35 |
| fatty acid | 15-56 |
| polyalkylene oxide | 20-50 |

IR spectra of functional layers can be recorded by pressing an ATR crystal onto the functional layer. Since the spectra are recorded in the ATR mode, the spectrum of a fiber corresponds to the spectrum of the functional layer. The functional layer has a characteristic absorption in the infrared range in the Fourier-Transform-Infrared-Attenuated-Total-Reflection (FTIR-ATR) spectrum. The IR spectrum of the functional layer on the fibers of the fiber articles of this invention, due to the unique composition, is characteristic. In particular, they differ from the IR spectra of the functional layers of the prior art. For example, the functional layers of this disclosure show—if at all—only very weak bands in the wave number range of about 1750 $cm^{-1}$ (±25 $cm^{-1}$), which can be ascribed to the absence of polyacrylates and polymethacrylates. The same applies to bands in the range of 1590 $cm^{-1}$ (±25 $cm^{-1}$), which can be ascribed to the absence of aromatic components. Many aromatic compounds are carcinogenic, and therefore not desired.

Preferably, the functional layer in the FTIR-ATR spectrum has a ratio of the maximum absorption band height in the range of 3200 $cm^{-1}$ to 3600 $cm^{-1}$ to the maximum absorption band height in the range of 3800 $cm^{-1}$ to 4000 $cm^{-1}$ of at least 1.3, preferably of at least 1.4, preferably of at least 1.5, preferably of at least 1.6, preferably of at least 1.7, preferably of at least 1.8, preferably of at least 1.9, preferably of at least 2.0, preferably of at least 2.1, preferably of at least 2.2. Preferably, the functional layer in the FTIR-ATR spectrum has a ratio of the maximum absorption band height in the range of 3200 $cm^{-1}$ to 3600 $cm^{-1}$ to the maximum absorption band height in the range of 3800 $cm^{-1}$ to 4000 $cm^{-1}$ of at most 35, preferably of at most 30, preferably of at most 25, preferably of at most 20, preferably of at most 15, preferably of at most 10, preferably of at most 9, preferably of at most 8, preferably of at most 7, preferably of at most 6. Preferably, the functional layer in the FTIR-ATR spectrum has a ratio of the maximum absorption band height in the range of 3200 $cm^{-1}$ to 3600 $cm^{-1}$ to the maximum absorption band height in the range of 3800 $cm^{-1}$ to 4000 $cm^{-1}$ of 1.3 to 35, preferably 1.4 to 30, preferably 1.5 to 25, preferably 1.6 to 6. The absorption described here is, for example, effected by an advantageous ratio of the functional silane and/or the optional polyvalent alcohol to the further components of the functional layer. If the relative absorption of 3200 $cm^{-1}$ to 3600 $cm^{-1}$ described here is too low, the ratio of the functional silane to the other components of the functional layer is too low. Hence, adhesion of the functional layer at the surface of the cladding layer is decreased. Furthermore, bonding ability of the functional layer with further layers, such as for example an adhesive layer in a combination of optical fiber bundles is reduced. In contrast, if the relative absorption of 3200 $cm^{-1}$ to 3600 $cm^{-1}$ described here is too high, the ratio of the functional silane to the other components of the functional layer is too high. This results in the fact that the friction between the optical fibers is increased and that sliding ability is reduced.

Preferably, the functional layer in the FTIR-ATR spectrum has a ratio of the maximum absorption band height in the range of 800 $cm^{-1}$ to 1200 $cm^{-1}$ to the maximum absorption band height in the range of 1500 $cm^{-1}$ to 1900 $cm^{-1}$ of at least 1.1, preferably of at least 1.2, preferably of at least 1.3, preferably of at least 1.4, preferably of at least 1.5, preferably of at least 1.6, preferably of at least 1.7, preferably of at least 1.8, preferably of at least 1.9, preferably of at least 2.0. Preferably, the functional layer in the FTIR-ATR spectrum has a ratio of the maximum absorption band height in the range of 800 $cm^{-1}$ to 1200 $cm^{-1}$ to the maximum absorption band height in the range of 1500 $cm^{-1}$ to 1900 $cm^{-1}$ of at most 300, preferably of at most 200, preferably of at most 100, preferably of at most 50, preferably of at most 30, preferably of at most 20, preferably of at most 10, preferably of at most 7, preferably of at most 6, preferably of at most 5. Preferably, the functional layer in the FTIR-ATR spectrum has a ratio of the maximum absorption band height in the range of 800 nm to 1200 nm to the maximum absorption band height in the range of 1500 $cm^{-1}$ to 1900 $cm^{-1}$ of 1.3 to 300, preferably 1.4 to 250, preferably 1.5 to 200, preferably 2.0 to 10. The absorption described here is, for example, effected by an advantageous ratio of the functional silane, the optional alkylsilane and/or the optional PEG silane, in particular, to undesired photopolymerizable and/or photopolymerized compounds. If the relative absorption of 800 $cm^{-1}$ to 1200 $cm^{-1}$ described here is too low, the ratio of photopolymerizable and/or photopolymerized compounds is too high. Such functional layers are not harmless to health.

Preferably, the functional layer in the FTIR-ATR spectrum has a ratio of the maximum absorption band height in the range of 2700 $cm^{-1}$ to 3000 $cm^{-1}$ to the maximum absorption band height in the range of 1500 $cm^{-1}$ to 1900 $cm^{-1}$ of at least 1.1, preferably of at least 1.2, preferably of at least 1.3, preferably of at least 1.4, preferably of at least 1.5, preferably of at least 1.6, preferably of at least 1.7, preferably of at least 1.8, preferably of at least 1.9, preferably of at least 2.0. Preferably, the functional layer in the FTIR-ATR spectrum has a ratio of the maximum absorption band height in the range of 2700 $cm^{-1}$ to 3000 $cm^{-1}$ to the maximum absorption band height in the range of 1500 $cm^{-1}$ to 1900 $cm^{-1}$ of at most 300, preferably of at most 200, preferably of at most 100, preferably of at most 50, preferably of at most 30, preferably of at most 20, preferably of at most 10, preferably of at most 7, preferably of at most 6, preferably of at most 5. Preferably, the functional layer in the FTIR-ATR spectrum has a ratio of the maximum absorption band height in the range of 2700 $cm^{-1}$ to 3000 $cm^{-1}$ to the maximum absorption band height in the range of 1500 to 1900 nm of 1.3 to 300, preferably 1.4 to 250, preferably 1.5 to 200, preferably 2.0 to 5. The absorption described here is, for example, effected by an advantageous ratio of the functional silane, the optional alkylsilane, the optional PEG silane and/or the optional fatty acid, in particular, to undesired photopolymerizable and/or photopolymerized compounds. If the relative absorption of 2700 $cm^{-1}$ to 3000 $cm^{-1}$ described here is too low, the ratio of photopolymerizable and/or photopolymerized compounds is too high. Such functional layers may have a negative influence on the health of a patient.

Preferably, the functional layer in the FTIR-ATR spectrum has a ratio of the maximum absorption band height in the range of 3200 $cm^{-1}$ to 3600 $cm^{-1}$ to the maximum absorption band height in the range of 1500 $cm^{-1}$ to 1900 $cm^{-1}$ of at least 1.1, preferably of at least 1.2, preferably of at least 1.3, preferably of at least 1.4, preferably of at least 1.5. Preferably, the functional layer in the FTIR-ATR spectrum has a ratio of the maximum absorption band height in the range of 3200 $cm^{-1}$ to 3600 $cm^{-1}$ to the maximum absorption band height in the range of 1500 to 1900 nm of at most 3.0, preferably of at most 2.5, preferably of at most 2.2, preferably of at most 2.0. Preferably, the functional layer in the FTIR-ATR spectrum has a ratio of the maximum absorption band height in the range of 3200 $cm^{-1}$ to 3600 $cm^{-1}$ to the maximum absorption band height in the range of 1500 $cm^{-1}$ to 1900 $cm^{-1}$ of 1.1 to 3, preferably 1.1 to 2.5, preferably 1.1 to 2.0, or 1.2 to 2.5. The absorption described here is, for example, effected by an advantageous ratio of the functional silane and/or the optional polyvalent alcohol, in particular, to the undesired photopolymerizable and/or photopolymerized compounds. If the relative absorption of 3200 $cm^{-1}$ to 3600 $cm^{-1}$ described here is too low, the ratio of photopolymerizable and/or photopolymerized compounds is too high. Such functional layers are not harmless to health.

Preferably, the functional layer in the FTIR-ATR spectrum has a ratio of the maximum absorption band height in the range of 800 $cm^{-1}$ to 1200 $cm^{-1}$ to the maximum absorption band height in the range of 2700 $cm^{-1}$ to 3000 $cm^{-1}$ of at least 1.1, preferably of at least 1.2, preferably of at least 1.3, preferably of at least 1.4. Preferably, the functional layer in the FTIR-ATR spectrum has a ratio of the maximum absorption band height in the range of 800 $cm^{-1}$ to 1200 $cm^{-1}$ to the maximum absorption band height in the range of 3200 $cm^{-1}$ to 3600 $cm^{-1}$ of at most 35, preferably of at most 30, preferably of at most 25, preferably of at most 20, preferably of a most 15, preferably of at most 10, preferably of at most 9.0, preferably of at most 5, preferably of at most 3.0, preferably of at most 2.0. Preferably, the functional layer in the FTIR-ATR spectrum has a ratio of the maximum absorption band height in the range of 800 $cm^{-1}$ to 1200 $cm^{-1}$ to the maximum absorption band height in the range of 3200 $cm^{-1}$ to 3600 $cm^{-1}$ of 1.1 to 35, preferably 1.2 to 15, preferably 1.3 to 2.0. The absorption described here is, for example, effected by an advantageous ratio of the functional silane and/or the optional polyvalent alcohol, in particular, to functional silane, optional alkylsilane and/or optional PEG silane. If the relative absorption of 800 nm to 1200 nm described here is too low, the proportion of functional silane is too low. If the relative absorption of 800 $cm^{-1}$ to 1200 $cm^{-1}$ described here is too high, then the proportion of functional silane is too high.

For a good sliding effect between optical fibers, without bonding them to one another, the functional layer should have suitable friction coefficients. The friction coefficient can be measured according to a method which is known by a person skilled in the art at the surface of the functional layer. The measurement may, for example, be conducted by moving an optical fiber article or a respective glass rod of the same material like the fiber article (test article) in an angle of 90° with respect to a friction partner which is also formed of an optical fiber article or a respective glass rod with a normal force Fn of 0.5 N with a speed of 10 mm/min. The movement is conducted in longitudinal direction, based on the test article. The friction partner is also formed of an optical fiber article or a respective glass rod. Here, depending on the friction value, a friction force is generated which is measured and used as a measure for the friction value (friction value=quotient of friction force and normal force). Preferably, the functional layer has a friction coefficient of at most 0.5, preferably of at most 0.45, preferably of at most 0.35, preferably of at most 0.3, preferably of at most 0.2, preferably of at most 0.15. Preferably, the functional layer has a friction coefficient of at least 0.001, preferably of at least 0.01, preferably of at least 0.03, preferably of at least 0.05. In preferable embodiments, the functional layer has a friction coefficient of 0.001 to 0.5, preferably of 0.01 to 0.35, preferably of 0.03 to 0.2. In preferable embodiments, the functional layer has a friction coefficient of less than 0.2. If the friction coefficient is too high, sliding of the optical fibers against each other is reduced, and it results in microcracks and fractures. If the friction coefficient is too low, cohesion of the optical fibers, for example in an optical fiber bundle, is reduced.

The surface of the functional layer should have a suitable contact angle for achieving good wettability of the optical fiber, for example with an adhesive in an assembly of optical fiber bundles. The contact angle can be measured at the surface of the functional layer according to a method which is known by a person skilled in the art (for example according to ISO DIN 55660-2:2011). Preferably, the functional layer has a contact angle of at least 10°, preferably of at least 20°, preferably of at least 40°, preferably of at least 60°, preferably of at least 80°. Preferably, the functional layer has a contact angle of at most 125°, preferably of at most 100°. In preferable embodiments, the functional layer has a contact angle of 20° to 120°, preferably of 40° to 100°, preferably of 60° to 100°. In preferable embodiments, the functional layer has a contact angle of 50° to 85°. If the contact angle is too small, the surface of the functional layer is too hydrophilic, and it results in a reduced chemical protection effect. If the contact angle is too large, wettability of the surface of the functional layer for example with an adhesive layer in an assembly is reduced.

The functional layer should adhere well to the surface of the fiber, it should allow a good, but limited, adhesion of the fibers among each other and it should allow a good bonding of a fiber article, in particular fiber bundle, to other materials, e.g. a sheath. The result achieved in the below described press test is a measure for the adhesion of the fibers to each other. In the press test, a fiber bundle or, for comparison, several, optionally different, fiber bundles with a diameter of 5 mm is/are glued with identical adhesive into one sheath of stainless steel each, for example with a two-component epoxy resin adhesive, preferably solvent-free and with crosslinking at room temperature (e.g. Araldit AY103-1 curing agent; REN HY 956, company Huntsman; curing at 60° C. for 2 h). The end face of the fiber bundles is ground and polished. With a test pin having a round cross-section, a diameter of 2.5 mm and a planar end face subsequently the forces required to destroy the bond (press force) are measured by pressing the test pin in fiber direction onto the fibers which are bonded in the sheath. The pressing speed is 6 mm/min. Two scenarios of failure arise. In the first case, the bond of the fiber bundle to the stainless steel sheath fails (the whole fiber bundle is pushed out of the sheath). In the second case, the fiber bond among the fibers fails. In the first case, adhesion of the fibers among each other is better than adhesion of the fiber bundle to the stainless steel sheath. In the second case, this indicates a poor adhesion of the adhesive to the glass fibers which shows an insufficient adhesive property of the functional layer. The detected maximum force required for moving the bonded fiber bundle being located below the test pin with respect to the stainless steel sheath and/or the circumjacent fibers is the press force.

Preferably, the optical fiber article has a press force of at least 250 N, preferably of at least 300 N, preferably of at least 350 N, preferably of at least 400 N, preferably of at least 500 N, at least 700 N or at least 900 N. In embodiments, the optical fiber article has a press force of at most 5,000 N, preferably of at most 4,500 N, preferably of at most 4,000 N, preferably of at most 3,500 N, preferably of at most 3,000 N. In preferable embodiments, the optical fiber article has a press force of 100 to 5,000 N, preferably of 150 to 4,500 N, preferably of 200 to 4,000 N. If the press force is too low, adhesion of the functional layer at the surface of the cladding layer is bad or the adhesion property of the functional layer is too weak.

Preferably, the optical fiber article comprises fibers having a high breaking length, in particular of at least 20 m. Further preferably, the fibers have a breaking length of at least 30 m, further preferably of at least 40 m, further preferably of at least 50 m, further preferably of at least 60 m, further preferably of at least 70 m, further preferably of at least 80 m, further preferably of at least 90 m. If the length is too small, then the optical fibers break too often, and they are not suitable for the use as light guide and/or image guide. Furthermore, broken optical fibers are a risk for health. The breaking length can be measured as follows: The test fiber is provided as a continuous fiber having a length of at least 2 km on a bobbin (e.g. Styrofoam standard bobbin having a circumference of 0.49 m). The fiber to be tested is subjected to a defined bending load by means of a pulling-bending device, wherein the fiber is rewound over 4 rolls having a radius of 6 mm. The test fiber which during this procedure is under permanent tension is unwound from a slowed down bobbin and wound up onto a second motor-driven bobbin. When the fiber breaks, then the unwinding process is stopped by a fracture indicating sensor. For the continuation of the measurement, the fiber is again applied. The breaking length is the fiber length at which the probability of fracture is 63% (Weibull distribution). For the calculation, preferably, at least 10 measurements, preferably 25 measurements are conducted. The test is conducted with a tensile force of 25+/−1 cN and a rewinding velocity of 25+/−1 U./min (corresponds to 12.5 m/min).

The optical fiber article should contain fibers which are characterized by a high mechanical stability and, if possible, do not fracture. The breaking tendency of the fibers can be measured in the breaking-loop test according to DIN 58141-6:2011. The test is used for the measurement of the basic strength of a fiber article. With this method, the mechanical bending radius of light guide fibers is determined by applying a load onto them until breakage of the fibers by means of a narrowing 360° loop (destructive test). The result of the breaking-loop test is a bending radius, thus a measure how strongly the fiber can be bent without breakage. The fibers of the optical fiber article, preferably, have a bending radius of less than 10 mm, in particular less than 5 mm, less than 3 mm or even less than 2 mm. In particular, the fibers are characterized by a very small bending radius even after hydrolytic stress. Preferably, also after storage of the fibers in water at 50° C. for 5 days, the bending radius of the fibers remains at less than 12 mm, less than 8 mm or less than 6 mm. The fact that the fibers widely maintain their good bending properties even in the case of hydrolytic stress is a huge advantage with respect to cleaning and sterilization of optical fiber articles.

Acrylates, methacrylates, vinyl and styrene compounds as well as other unsaturated compounds which cure, when irradiated with UV, are a potential risk for the environment and may damage the health of human beings. Therefore, the functional layer should have a proportion of photopolymerizable and/or photopolymerized substances as low as possible.

Preferably, the optical fiber article has a content of photopolymerized polymers in the functional layer, based on the mass of the functional layer, of less than 1% by weight, preferably of less than 4% by weight, preferably of less than 3% by weight, preferably of less than 2% by weight, preferably of less than 1% by weight, preferably of less than 0.8% by weight, preferably of less than 0.6% by weight, preferably of less than 0.4% by weight, preferably of less than 0.2% by weight, preferably of less than 0.1% by weight, preferably of less than 0.05% by weight, preferably of less than 0.01% by weight, preferably of less than 0.005% by weight, preferably of less than 0.001% by weight. In preferable embodiments, the functional layer is free of photopolymerized polymers. "Photopolymerized polymers" means polymers which can be produced by polymerization of UV curable mono- or oligomers. Photopolymerized polymers which are preferably avoided according to the present disclosure are, for example, polyacrylates, polymethacrylates, polyvinyl polymers, polystyrene and/or derivatives thereof. If the proportion of photopolymerized polymers in the functional layer is too high, the optical fiber article is a potential risk for health. In particular, in the case of medical apparatuses which are often autoclaved it may be that photopolymerized polymers release residual monomers or photoinitiators. In particular, in the case of medical apparatuses which come in contact with human organs, such as for example endoscopes, the proportion of photopolymerized polymers should not be higher than described here. In particular, also the content of photopolymerizable mono- and/or oligomers in the functional layer should be low. In particular, the content of acrylates, methacrylates, styrene and vinyl compounds in the functional layer is preferably limited to less than 1% by weight, less than 0.1% by weight or less than 0.01% by weight.

Photoinitiators may cause risks for the health of human beings. In preferable embodiments, the optical fiber article has a content of photoinitiators and/or derivatives thereof in the functional layer, based on the mass of the functional layer, of less than 5% by weight, preferably of less than 4% by weight, preferably of less than 3% by weight, preferably of less than 2% by weight, preferably of less than 1% by weight, preferably of less than 0.8% by weight, preferably of less than 0.6% by weight, preferably of less than 0.4% by weight, preferably of less than 0.2% by weight, preferably of less than 0.1% by weight, preferably of less than 0.05% by weight, preferably of less than 0.01% by weight, preferably of less than 0.005% by weight, preferably of less than 0.001% by weight. In preferable embodiments, the functional layer is free of photoinitiators and/or derivatives thereof. "Photoinitiators and/or derivatives thereof" means chemical compounds which after absorption of photons, such as for example UV light, form reactive species which can start a reaction, such as for example a polymerization. Photoinitiators and/or derivatives thereof may also mean the compounds thereof which are the result of an already occurred reaction. Photoinitiators according to the present disclosure may include, for example, radical photoinitiators, cationic photoinitiators and/or thermo-latent photoinitiators. Such photoinitiators may include, for example, acylphosphine oxides, alpha-alkoxy aryl ketones or aryldiazoniums or combinations thereof. If the proportion of photoinitiators and/or derivatives thereof in the functional layer is too high, the optical fiber article is a potential risk for health. In particular, in the case of medical apparatuses, this is not desired.

The functional layer should be dried well, and it should have a low water content. Preferably, the optical fiber article has a content of residual water in the functional layer, based on the mass of the functional layer, of less than 5% by weight, preferably of less than 4% by weight, preferably of less than 3% by weight, preferably of less than 2% by weight, preferably of less than 1% by weight, preferably of less than 0.8% by weight, preferably of less than 0.6% by weight, preferably of less than 0.4% by weight, preferably of less than 0.2% by weight, preferably of less than 0.1% by weight, preferably of less than 0.05% by weight, preferably of less than 0.01% by weight, preferably of less than 0.005% by weight, preferably of less than 0.001% by weight. In preferable embodiments, the functional layer is free of water. If the proportion of water is too high, the isolating protection effect of the functional layer is reduced and the mechanical and chemical stability of the optical fiber article is reduced.

The functional layer should be dried well, and it should have a low content of residual water-miscible solvents. Such solvents are, in particular, aliphatic ethers or alcohols with up to 10 carbon atoms and/or carboxylic acids with up to 6 carbon atoms. Examples for water-miscible solvents are acetic acid, ethanol, isopropanol, dipropylene glycol monomethyl ether or tripropylene glycol monomethyl ether. Preferably, the optical fiber article has a content of residual water-miscible solvents in the functional layer, based on the mass of the functional layer, of less than 5% by weight, preferably of less than 4% by weight, preferably of less than 3% by weight, preferably of less than 2% by weight, preferably of less than 1% by weight, preferably of less than 0.8% by weight, preferably of less than 0.6% by weight, preferably of less than 0.4% by weight, preferably of less than 0.2% by weight, preferably of less than 0.1% by weight, preferably of less than 0.05% by weight, preferably of less than 0.01% by weight, preferably of less than 0.005% by weight, preferably of less than 0.001% by weight. In preferable embodiments, the functional layer is free of water-miscible solvents. If the proportion of water-miscible solvents is too high, the isolating protection effect of the functional layer is reduced and the mechanical and chemical stability of the optical fiber article is reduced.

In preferable embodiments, the optical fiber article has a content of residual short-chain carboxylic acids having up to 10 carbon atoms in the functional layer, based on the mass of the functional layer, of less than 5% by weight, preferably of less than 4% by weight, preferably of less than 3% by weight, preferably of less than 2% by weight, preferably of less than 1% by weight, preferably of less than 0.8% by weight, preferably of less than 0.6% by weight, preferably of less than 0.4% by weight, preferably of less than 0.2% by weight, preferably of less than 0.1% by weight, preferably of less than 0.05% by weight, preferably of less than 0.01% by weight, preferably of less than 0.005% by weight, preferably of less than 0.001% by weight. Such short-chain carboxylic acids are, for example, acetic acid or citric acid. In preferable embodiments, the functional layer is free of short-chain carboxylic acids having up to 10 carbon atoms.

In preferable embodiments, the optical fiber article has a content of residual aliphatic alcohols having up to four carbon atoms in the functional layer, based on the mass of the functional layer, of less than 5% by weight, preferably of less than 4% by weight, preferably of less than 3% by weight, preferably of less than 2% by weight, preferably of less than 1% by weight, preferably of less than 0.8% by weight, preferably of less than 0.6% by weight, preferably of less than 0.4% by weight, preferably of less than 0.2% by weight, preferably of less than 0.1% by weight, preferably of less than 0.05% by weight, preferably of less than 0.01% by weight, preferably of less than 0.005% by weight, preferably of less than 0.001% by weight. Such short-chain carboxylic acids are, for example, ethanol or isopropanol. In preferable embodiments, the functional layer is free of aliphatic alcohols having up to four carbon atoms.

The optical fiber article should be well suitable for the use in medical apparatuses, such as for example endoscopes. For the medical use, the optical fiber article should be durable as long as possible, also in the case of frequent autoclaving. For that it is important that the optical fiber article contains as few halogens as possible. Preferably, the optical fiber article has a content of halogens in the functional layer, based on the functional layer, of less than 500 ppm (m/m), preferably of less than 400 ppm (m/m), preferably of less than 300 ppm (m/m), preferably of less than 250 ppm (m/m), preferably of less than 200 ppm (m/m), preferably of less than 150 ppm (m/m), preferably of less than 100 ppm (m/m), preferably of less than 80 ppm (m/m), preferably of less than 60 ppm (m/m), preferably of less than 40 ppm (m/m), preferably of less than 20 ppm (m/m), preferably of less than 10 ppm (m/m). In preferable embodiments, the functional layer is free of halogen. Halogens are, for example, chlorine, fluorine, bromine and/or iodine, and their anions. The term "halogen", in particular, comprises the halides, preferably also other halogen compounds. Too high a concentration of halogens in the functional layer results in formation of respective halogen acids for example in the case of steam sterilization. The respective halogen acids may compromise durability of the optical fiber article, and they may be released from it. In particular, the halogen acids attack materials, such as for example stainless steel of autoclaves and endoscopes, and they result in the formation of undesired rust.

In particular, a content of residual chloride in the functional layer may result in the formation of hydrochloric acid. Therefore, the optical fiber article should comprise chloride in an amount as low as possible. Preferably, the optical fiber article has a content of chloride in the functional layer, based on the functional layer, of less than 500 ppm (m/m), preferably of less than 400 ppm (m/m), preferably of less than 300 ppm (m/m), preferably of less than 250 ppm (m/m), preferably of less than 200 ppm (m/m), preferably of less than 150 ppm (m/m), preferably of less than 100 ppm (m/m), preferably of less than 80 ppm (m/m), preferably of less than 60 ppm (m/m), preferably of less than 40 ppm (m/m), preferably of less than 20 ppm (m/m), preferably of less than 10 ppm (m/m). In preferable embodiments, the functional layer is free of chloride. Too high a content of chloride compromises corrosion resistance of the optical fiber article.

For suitability of the optical glass fiber article in medical and/or diagnostic applications, the optical glass fiber article should be biocompatible. Preferably, the fiber article is biocompatible according to ISO10993-1:2018. Preferably, the optical fiber article is biocompatible in the cytotoxicity test according to ISO10993-5:2009.

Preferably, the optical fiber article is biocompatible according to ISO10993-1:2018 and/or ISO10993-5:2009. Preferably, the optical fiber article is biocompatible according to USP Class VI.

The optical fiber article should only comprise compounds which, as far as possible, are not a risk for the health of human beings. For example, human beings come in contact with the optical fiber article during production and processing. Preferably, the optical fiber article has a proportion of compounds with a maximum admissible workplace concentration (MAC value) of less than 240 mg*m$^{-3}$ in the functional layer, based on the mass of the functional layer, of less than 5% by weight, preferably of less than 4% by weight, preferably of less than 3% by weight, preferably of less than 2% by weight, preferably of less than 1% by weight, preferably of less than 0.8% by weight, preferably of less than 0.6% by weight, preferably of less than 0.4% by weight, preferably of less than 0.2% by weight, preferably of less than 0.1% by weight, preferably of less than 0.05% by weight, preferably of less than 0.01% by weight, preferably of less than 0.005% by weight, preferably of less than 0.001% by weight.

Preferably, the optical fiber comprises a fiber core and a cladding or a cladding layer, wherein the functional layer is arranged on the cladding layer. In preferable embodiments, the core layer consists of a core glass. In other embodiments, the fiber core consists of a core polymer.

Suitable core polymers are, for example, polyacrylate, polymethacrylate, polyurethane, polyester, polyamide and mixtures thereof. The core glass may be a multicomponent glass, wherein, in particular, the core glass may comprise a combination of several oxides, thus it can be an oxidic glass. Basically, quartz glass is also suitable as core glass, but in contrast to the multicomponent glasses it has a very high melting point which makes the processing more difficult and, in particular, more energy-intensive.

Preferably, the optical fiber comprises a cladding layer which encloses the fiber core. In preferable embodiments, the cladding layer comprises a cladding glass. The cladding glass may be a multicomponent glass, wherein, in particular, the cladding glass may comprise a combination of several oxides, thus it can be an oxidic glass. In other embodiments, the cladding layer comprises a cladding polymer. Cladding polymers according to the present invention are, for example, polyacrylate, polymethacrylate, polyurethane, polyester, polyamide and mixtures thereof.

In certain embodiments, the optical fiber is a quartz fiber. In a certain embodiment, the cladding layer and/or the fiber core comprises a proportion of at least 76% by weight of quartz, preferably at least 81% by weight, preferably at least 84% by weight, preferably at least 88% by weight, preferably at least 92% by weight, preferably at least 95% by weight, preferably at least 97% by weight, preferably at least 98% by weight. A higher proportion of quartz results in an increased chemical resistance as well as in an increased temperature resistance.

In a certain embodiment, the core glass is characterized by the following features: Preferably, the core glass comprises at least 8% by weight of $SiO_2$, further preferably at least 23% by weight, more preferably at least 24% by weight and particularly preferably at least 25% by weight or even at least 26% by weight. In a particular embodiment, the core glass may contain at least 28.3% by weight of $SiO_2$, preferably at least 34% by weight of $SiO_2$. In some preferred embodiments, the core glass comprises at least 35% by weight of $SiO_2$, preferably at least 42% by weight.

Preferred core glasses of this disclosure have the following composition in % by weight:

| Component | min | max |
|---|---|---|
| $B_2O_3$ | 0 | 24 |
| $SiO_2$ | 23 | 62.1 |
| $Al_2O_3$ | 0 | 10 |
| $Li_2O$ | 0 | 10 |
| $Na_2O$ | 0 | 18.5 |
| $K_2O$ | 0 | 25.7 |
| BaO | 0 | 57.8 |
| ZnO | 0 | 40 |
| $La_2O_3$ | 0 | 25 |
| $ZrO_2$ | 0 | 10 |
| $HfO_2$ | 0 | 14.2 |
| $SnO_2$ | >0 | 2 |
| MgO | 0 | 8 |
| CaO | 0 | 8 |
| SrO | 0 | 24.4 |
| $Ta_2O_5$ | 0 | 22 |
| $Y_2O_3$ | 0 | 11.9 |
| $Rb_2O$ | 0 | 15 |
| $Cs_2O$ | 0 | 21 |
| $GeO_2$ | 0 | 7.5 |
| F | 0 | 2 |
| Σ $R_2O$ | 5 | 20 |
| Σ MgO, CaO, SrO, ZnO | 20 | 42 |

$R_2O$ is the sum of the contents of all alkali metal oxides.

One or more of the following components may be contained in the core glass?: $Cs_2O$, $Rb_2O$, MgO, CaO, SrO, $Gd_2O_3$, $Lu_2O_3$, $Sc_2O_3$, $Y_2O_3$, $In_2O_3$, $Ga_2O_3$ and $WO_3$.

The following components should preferably not be contained in the core glass or they should only be contained in concentrations which cannot be avoided due to impurities of the raw materials: $TiO_2$, $CeO_2$, $Nb_2O_5$, $MoO_3$, $Bi_2O_3$, PbO, CdO, $Tl_2O$, $As_2O_3$, $Sb_2O_3$, $SO_3$, $SeO_2$, $TeO_2$, BeO, radioactive elements and coloring components, unless otherwise described herein. In particular, $TiO_2$ should be omitted, because this component may result in strong absorption in the UV range. In preferable embodiments, also the component $WO_3$ is not present.

In an embodiment, the components $TiO_2$, $CeO_2$, $Nb_2O_5$ and/or $Bi_2O_3$ may be contained in the core glass in amounts of up to a maximum of 0.5% by weight, preferably up to 0.3% by weight and particularly preferably up to 0.2% by weight. In a preferred embodiment, the core glass is free of these components.

Preferably, the core glass is free of optically active components, in particularly $Sm_2O_3$, $Nd_2O_3$, $Dy_2O_3$, $Pr_2O_3$, $Eu_2O_3$, $Yb_2O_3$, $Tb_2O_3$, $Er_2O_3$, $Tm_2O_3$ and/or $Ho_2O_3$. $CeO_2$ absorbs in the UV range, so that preferred core glasses do not contain $CeO_2$.

The content of the components alkaline earth metal oxides, $La_2O_3$, $Ta_2O_5$, $ZrO_2$ and $HfO_2$ in sum is preferably, and in particular for core glasses having refractive values of higher than 1.65, at least 40% by weight, preferably at least 42% by weight, more preferably at least 50% by weight and preferably at least 55% by weight. If the content of these components is too low, the preferred refractive index normally cannot be achieved. Due to formulation reasons, this sum should not exceed a value of 72% by weight.

In a certain embodiment, the cladding glass has the following features:

Preferably, the cladding glass has a content of $SiO_2$ of >60% by weight, preferably >65% by weight and preferably of at least 69% by weight. Preferably, the $SiO_2$ content is at most 75% by weight and preferably up to 73% by weight. In principle, the cladding glass is more strongly influenced by the environment than the core glass. A high $SiO_2$ content imparts better chemical resistance. Thus, the content of this component in the cladding glass is preferably higher than in the core glass.

The coefficient of thermal expansion (CTE) in a temperature range of 20 to 300° C. may be the same or different for the fiber core and the cladding. In particular, the CTE is different. Preferably, the CTE of the cladding is lower than the CTE of the fiber core, preferably it is lower by at least $1.0*10^{-6}$/K or preferably by at least $2.5*10^{-6}$/K. Preferably, the fiber core has a CTE of $6.5*10^{-6}$ to $10*10^{-6}$/K, the cladding has a CTE of $4.5*10^{-6}$ to $6*10^{-6}$/K.

The following table shows some preferred compositions of cladding glasses which can be used together with the core glasses. The cladding glasses contain (in % by weight on oxide basis):

| Oxides | Group 1 | Group 2 | Group 3 | Group 4 |
| --- | --- | --- | --- | --- |
| $SiO_2$ | 70-78 | 63-75 | 75-85 | 62-70 |
| $Al_2O_3$ | 5-10 | 1-7 | 1-5 | 1-10 |
| $B_2O_3$ | 5-14 | 0-3 | 10-14 | >15 |
| $Li_2O$ | free | 0-1 | 0-3 | <0.1 |
| $Na_2O$ | 0-10 | 8-20 | 2-8 | 0-10 |
| $K_2O$ | 0-10 | 0-6 | 0-1 | 0-10 |
| MgO | 0-1 | 0-5 | free | 0-5 |
| CaO | 0-2 | 1-9 | free | 0-5 |
| SrO | 0-1 | free | free | 0-5 |
| BaO | 0-1 | 0-5 | free | 0-5 |
| halogen | free | free | free | free |

As core and/or cladding glass also chalcogenide glasses can be used, in particular the glasses which are disclosed in DE 4011553 C1 and EP 0 217 195 A1, the contents of which are incorporated herein by reference.

The optical fiber article may comprise one or more optical fibers. Here, the optical fibers can be present in an assembly in an unordered manner or can be arranged in optical fiber bundles. The optical fiber article may comprise one or more optical fiber bundles. Here, the optical fiber bundles can be present in an assembly in an unordered manner or can be arranged in fiber bundle groups. The optical fiber article may comprise one or more of optical fiber bundle groups.

In embodiments, the optical fiber article comprises at least one optical fiber, preferably at least two optical fibers, preferably at least three optical fibers, preferably at least five optical fibers, preferably at least seven optical fibers, preferably at least nine optical fibers, preferably at least ten optical fibers, preferably at least eleven optical fibers. In preferable embodiments, the optical fiber article comprises at least 15 optical fibers, preferably at least 50 optical fibers, preferably at least 100 optical fibers, preferably at least 300 optical fibers, preferably at least 700 optical fibers, preferably at least 1,600 optical fibers, preferably at least 2,800 optical fibers, preferably at least 4,700 optical fibers.

With adhesives optical fiber bundles can, for example, be combined together to larger assemblies and/or can be embedded in sheaths. In preferred embodiments, the optical fiber article does not comprise an adhesive layer. In an embodiment, the optical fiber article, in addition to the functional layer, comprises one or more adhesives which can be arranged at or in the functional layer. Then, at least partially, the optical fiber article can comprise the reaction product of the functional silane with a reactive adhesive component. Preferably, not the whole optical fiber article is bonded with an adhesive, but only a portion of the article comprises the reaction product of functional silane and at least one adhesive. In an embodiment, the optical fiber article comprises one or more adhesives at or in the functional layer only in a length of at most 25 mm, in particularly at most 15 mm or at most 10 mm. If too large a section of the optical fiber article is bonded using an adhesive, the risk of fracture of the fiber increases. In an embodiment, the optical fiber article comprises one or more adhesives at or in the functional layer in a length of at least 1 mm, in particularly at least 3 mm.

Adhesives which can be used according to the present disclosure and with which optical fibers can be bonded to one another or with other materials are, for example, epoxy resin adhesives, acrylate adhesives, cyan adhesives, polyurethane adhesives, silicone adhesives, phenol resin adhesives, polysulfide adhesives and/or bismaleimide adhesives. In embodiments, the fiber article comprises less than 10% by weight of adhesive, preferably less than 8% by weight, preferably less than 6% by weight, preferably less than 4% by weight, preferably less than 2% by weight, preferably less than 1% by weight, preferably less than 0.8% by weight, preferably less than 0.6% by weight, preferably less than 0.4% by weight, preferably less than 0.1% by weight.

Preferably, the optical fiber article comprises a proportion of the functional layer of the optical fiber of at most 10% by weight, preferably of at most 8% by weight, preferably of at most 6% by weight, preferably of at most 4% by weight, preferably of at most 2% by weight, preferably of at most 1% by weight, preferably of at most 0.5% by weight, preferably of at most 0.2% by weight, preferably of at most 0.1% by weight. Preferably, the optical fiber article comprises a proportion of the functional layer of the optical fiber of at least 0.001% by weight, preferably of at least 0.005% by weight, preferably of at least 0.009% by weight, preferably of at least 0.012% by weight, preferably of at least 0.02% by weight, preferably of at least 1% by weight, preferably of at least 0.04% by weight, preferably of at least 0.06% by weight, preferably of at least 0.08% by weight. In preferred embodiments, the optical fiber article comprises a proportion of the functional layer of the optical fiber of 0.001 to 10% by weight, further preferably of 0.005 to 8% by weight, further preferably of 0.009 to 6% by weight. If the proportion of the functional layer is too low, then the mechanical and chemical as well as thermal stability of the optical fiber is compromised. If the proportion of the functional layer is too high, cohesion of the optical fibers, for example in an optical fiber bundle, is reduced.

Preferably, the functional layer has a thickness of at least 0.1 nm, preferably at least 0.9 nm, preferably at least 1.2 nm, preferably at least 1.5 nm, preferably at least 1.8 nm, preferably at least 2.1 nm, preferably at least 3 nm. Preferably, the functional layer has a thickness of at most 500 nm, preferably of at most 200 nm, preferably of at most 100 nm, preferably of at most 50 nm, preferably of at most 20. If the thickness of the functional layer is too low, mechanical and chemical as well as thermal stability of the optical fiber is compromised. If the thickness of the functional layer is too high, cohesion of the optical fibers, for example in an optical fiber bundle, is reduced.

Preferably, the optical fiber comprises at least one functional layer. In embodiments, the optical fiber comprises at least two functional layers, at least three functional layers or at least four functional layers. Multiple functional layers increase the bending load capacity of the optical fiber and increase the protection from microcracks.

Preferably, a method for the production of an optical fiber article comprises the steps:
a. providing at least one optical fiber;
b. coating at least a part of the optical fiber with a size,
c. drying the size.

The optical fiber can, for example, be provided by a drawing method which is known by a person skilled in the art, such as for example from a preform, or in the nozzle method.

The coating of the optical fiber can be conducted according to a method which is known by a person skilled in the art, for example in an immersion tank, by spraying of the fiber or in a roll-to-roll method.

The dried size forms the functional layer. The drying of the size influences the properties of the functional layer. The functional layer is preferably dried in the presence of a gas mixture. In preferable embodiments, the gas mixture is air.

The air humidity of the gas mixture influences the drying and the material properties of the functional layer. The term "air humidity" or "air moisture" means the relative air humidity. Preferably, the gas mixture has an air humidity of at least 10%, preferably of at least 15%, preferably of at least 20%, preferably of at least 25%, preferably of at least 30%, preferably of at least 35%. Preferably, the gas mixture has an air humidity of at most 95%, preferably of at most 85%, preferably of at most 75%, preferably of at most 60%, preferably of at most 55%. In preferred embodiments, the gas mixture has an air humidity of 10% to 95%, of 15% to 85% or of 20% to 60%. If the air moisture of the gas mixture is too low, then, in particular, the functional silane and/or the optional alkylsilane and/or the optional PEG silane react with the surface of the fiber less reliably. Hence, adhesion of the functional layer to the fiber is decreased. If the air moisture of the gas mixture is too high, the size dries too slowly, and this compromises the mechanical and chemical resistance of the optical fiber. Furthermore, too high an air moisture results in too high a content of residual water and/or residual water-miscible solvents in the functional layer.

The temperature influences drying and the material properties of the functional layer. The temperature means the temperature of the gas mixture which surrounds the fiber during drying and/or of an optional contact surface with which a fiber may be in contact during drying, e.g. a heated or not heated bobbin and/or other fibers. Preferably, during drying the fiber is subjected to a temperature of at most 120° C., preferably of at most 100° C., preferably of at most 80° C., preferably of at most 50° C., preferably of at most 40° C., preferably of at most 30° C. Preferably, during drying the fiber is subjected to a temperature of at least 8° C., preferably of at least 15° C., preferably of at least 18° C., preferably of at least 20° C., preferably of at least 21° C., preferably of at least 22° C. In preferred embodiments, during drying the fiber is subjected to a temperature of 8 to 120° C., preferably of 15 to 100° C., preferably of 18 to 30° C. If the temperature of the gas mixture during drying is too high, this results in undesired chemical side reactions and undesired byproducts. Furthermore, too high a temperature of the gas mixture during drying results in a decreased adhesion of the functional layer to the surface of the fiber. If the temperature of the gas mixture during drying is too low, the size dries too slowly, and this compromises the mechanical chemical resistance of the optical fiber and it also results in too high a content of residual water and/or residual aqueous solvents in the functional layer.

Often, sizes are irradiated with UV radiation for curing. However, preferably, the optical fiber article is not subjected to a curing process and is not dried by UV radiation.

In an embodiment, the method comprises the treatment of the dried size (dry size) with a liquid component for obtaining a wet size as functional layer, wherein the liquid component at 1013 hPa has a boiling point of higher than 100° C. or higher than 200° C. The liquid component may be selected from the group consisting of silicone oil, polyethylene glycol, alcohols (e.g. long-chain or multivalent), esters, ethers, ketones, acetates and combinations thereof. Typically, the dry size comprises less than 50% by weight, in particular less than 35% by weight of the liquid component. Preferably, the wet size comprises at least 35% by weight, in particular at most 85% by weight of the liquid component. In an embodiment, the proportion of the liquid component of the wet size is between 35 and 65% by weight.

Also an optical fiber article with such a wet size as functional layer is part of this disclosure, which can in particular be prepared according to the method described herein. The optical fiber article with wet size can be characterized by the features which are described as advantageous herein, with the proviso that the functional layer comprises a proportion of at least 35% by weight of the liquid component described for the wet size.

When glass fiber bundles are processed, a distinction is made between so-called dry and wet sizes as functional layer. In the case of wet sizes, the single fibers in the bundle easily stick together. Thus, it can be achieved that the single fibers fan out less strongly and are also electrostatically charged less strongly. Hence, it can be achieved that, for example, the threading of the fiber bundles into sheaths can be facilitated considerably which helps reduce the assembly/installation effort. In particular, increased fiber packing densities can be achieved which improves transmission of luminous flux. In addition, a simplified assembly/installation is achieved, in particular in the case of relatively long light guides.

However, when dry sizes are used, the single fibers stick together less strongly. This is an advantage, when, for example, the single fibers have to be separated and/or have to be mixed in the bundle (this is also referred to as "randomization process"), for achieving a more homogenous illumination, or, in the case of multi-arm bundles, when the fibers of the single arms have to be installed in a common end sheath as uniform as possible, i.e. statistically well distributed. In the latter case, a wet size would rather be obstructive.

It is advantageous that at first a dry size can be provided as a functional layer on the fiber article. Only by the addition of a liquid component which is a liquid with high boiling point, preferably >100° C., more preferably >200° C., in a customized and/or application-specific manner a wet size can be provided from the dry size which is connected with considerable advantages in the production process. In principle, it is imaginable, at first, to apply a dry size onto the fiber article and, when needed, to add the liquid component in a subsequent coating process. Hence, depending on the wish of the customer and/or depending on the use, it is possible to adjust the property of the size in a targeted manner. Here, the liquid component may be composed of at least one of the following constituents: silicone oil, polyethylene glycol, alcohols (e.g. long-chain or multivalent), esters, ethers, ketones, acetates and combinations thereof. The concentration of the liquid component in the functional layer on the fiber article in the case of a dry size is typically lower than 50% by weight, preferably lower than 35% by weight. In the case of a wet size the proportion is at least 35% by weight, typically in the range of 35 to 65% by weight.

Preferably, the optical fiber article is used in a fiber bundle as light guide and/or image guide. For example, the optical fiber article can be used in endoscopes, inspection cameras, microscopes and/or spectroscopes.

Preferably, the optical fiber article is used in a diagnostic or therapeutic method. For example, the optical fiber article can be used in the field of endoscopy and/or operations with flexible inspection cameras.

EXAMPLES

Example E1

For the preparation of a size solution the following components (from Sigma Aldrich each) were added to a solution of ethanol, completely demineralized water and acetic acid in a 1 L laboratory glass bottle and stirred for at least one hour on a usual laboratory magnetic stirrer plate.

| Component | Amount |
|---|---|
| stearic acid | 1.8 g |
| polyethylene glycol 40 | 2 g |
| octyl trimethoxy silane | 1.2 g |
| N-[3-(trimethoxysilyl)propyl]ethylenediamine | 0.55 g |

Examples E2-E22

For the preparation of size solutions the components which are shown in table 1, table 2 and table 3 (all obtained from Sigma Aldrich) were added to a solution of ethanol, completely demineralized water, optional acetic acid and optional further solvents, such as for example dipropylene glycol monomethyl ether or tripropylene glycol monomethyl ether, in a 1 L laboratory glass bottle and stirred for at least one hour on a usual laboratory magnetic stirrer plate. Table 1 shows the components without solvents such as ethanol, completely demineralized water or acetic acid in relative % by weight of the examples E2-E22. PEG-Si=2-[methoxy(polyethyleneoxy)9-12propyl]trimethoxysilane, Ami-Si=N-[3-(trimethoxysilyl)propyl]ethylenediamine, Alk-Si=trimethoxy(octyl)silane. Subsequently, the size solution was applied onto optical fibers by the roll-to-roll method and dried at room temperature. Table 1 also shows the press force and the information, whether in the press test the connection fiber-sheath (F-S) or the connection fiber-fiber (F-F) has failed. Furthermore, the breaking length is given.

TABLE 1

| | Example | | | | | | |
|---|---|---|---|---|---|---|---|
| | E2 | E3 | E4 | E5 | E6 | E7 | E8 |
| PEG-Si | 60.64 | 60.60 | 60.61 | | | | |
| Ami-Si | 39.36 | 39.40 | 39.39 | 35.95 | 32.39 | 15.75 | 10.50 |
| Alk-Si | | | | | | 17.61 | 34.25 | 22.83 |
| PEG400 | | | | 64.05 | 50.00 | | 33.33 |
| stearic acid | | | | | | 50.00 | 33.33 |
| glycerin | | | | | | | |
| diethylene glycol | | | | | | | |
| 1,5-pentanediol | | | | | | | |
| press force [N] | 1250 | 1250 | 1300 | 650 | — | — | 750 |
| failure | F_H | F-H | F-H | F-H | — | — | F-H |
| breaking length [m] | | | | | 350 | 620 | |

TABLE 2

| | Example | | | | | | |
|---|---|---|---|---|---|---|---|
| | E9 | E10 | E11 | E12 | E13 | E14 | E15 |
| PEG-Si | | | | | | | |
| Ami-Si | 12.65 | 14.17 | 10.56 | 4.35 | 2.74 | 7.92 | 6.52 |
| Alk-Si | 27.50 | 30.81 | 22.97 | 9.46 | 5.96 | 17.21 | 14.19 |
| PEG400 | 40.15 | 44.98 | 33.54 | 13.81 | 8.71 | 49.74 | 58.58 |
| stearic acid | 19.71 | 10.05 | | 13.81 | 8.71 | 25.13 | 20.71 |
| glycerin | | | 32.93 | 58.58 | 73.88 | | |
| diethylene glycol | | | | | | | |
| 1,5-pentanediol | | | | | | | |
| press force | 750 | 700 | — | — | — | 1400 | 1500 |
| failure | F-H | F-H | — | — | — | F-H | F-H |

TABLE 3

| | Example | | | | | | |
|---|---|---|---|---|---|---|---|
| | E16 | E17 | E18 | E19 | E20 | E22 | E22 |
| PEG-Si | | | | | | | |
| Ami-Si | 5.55 | 2.37 | 10.06 | 4.35 | 2.74 | 4.35 | 2.74 |
| Alk-Si | 12.07 | 5.15 | 21.88 | 9.46 | 5.96 | 9.46 | 5.96 |
| PEG400 | 64.77 | 21.24 | 36.13 | 13.81 | 8.71 | 13.81 | 8.71 |
| stearic acid | 17.62 | 7.51 | 31.94 | 13.81 | 8.71 | 13.81 | 8.71 |
| glycerin | | 63.73 | | | | | |
| diethylene glycol | | | | 58.58 | 73.88 | | |
| 1,5-pentanediol | | | | | | 58.58 | 73.88 |
| press force | 1150 | 900 | — | — | — | — | — |
| failure | F-H | F-H | — | — | — | — | — |

Figure 2:
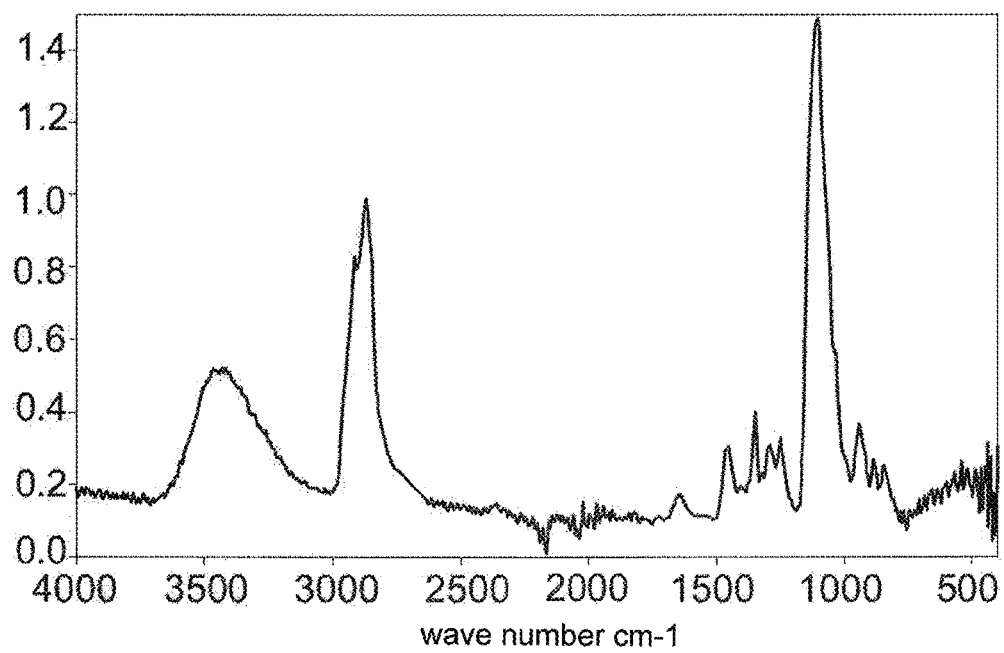
FIG. 2 shows the FTIR-ATR spectrum of example E14.
Figure 3:
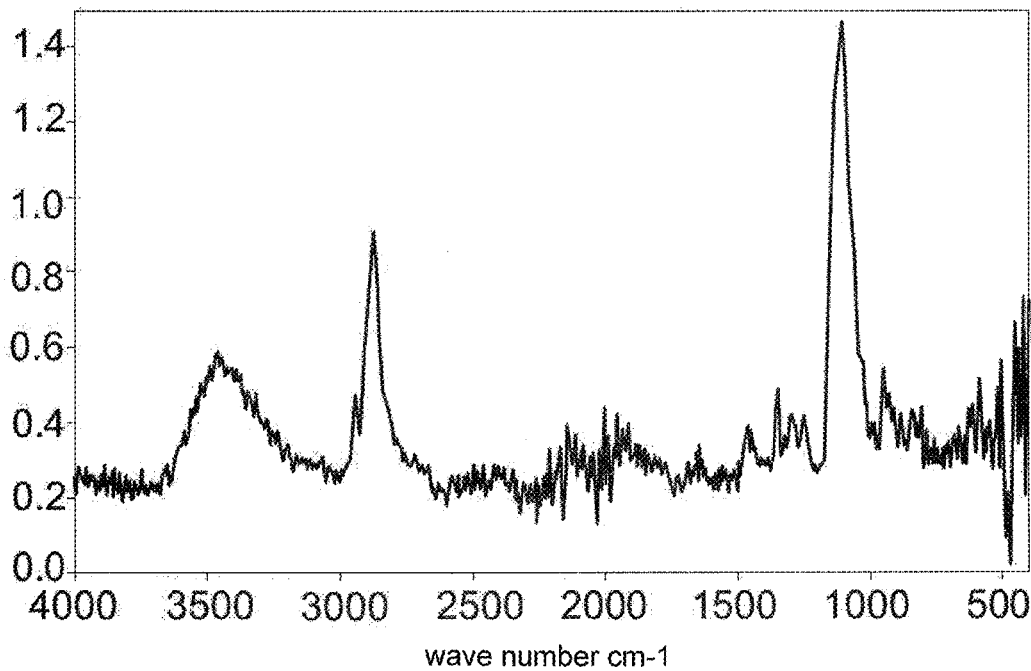
FIG. 3 shows the FTIR-ATR spectrum of example E18.
Figure 4:
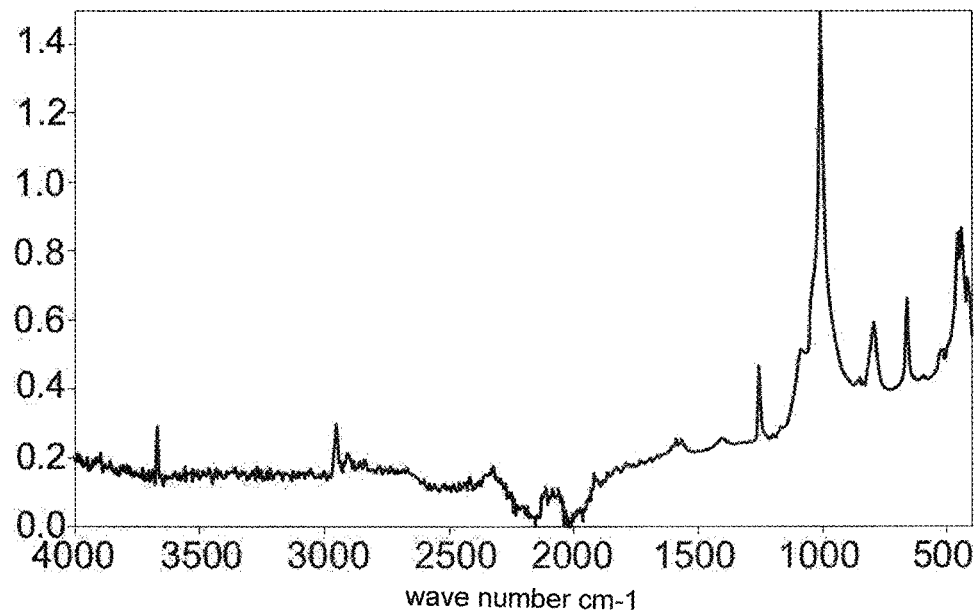
FIG. 4 shows the FTIR-ATR spectrum of a commercially available fiber article.
Figure 5:
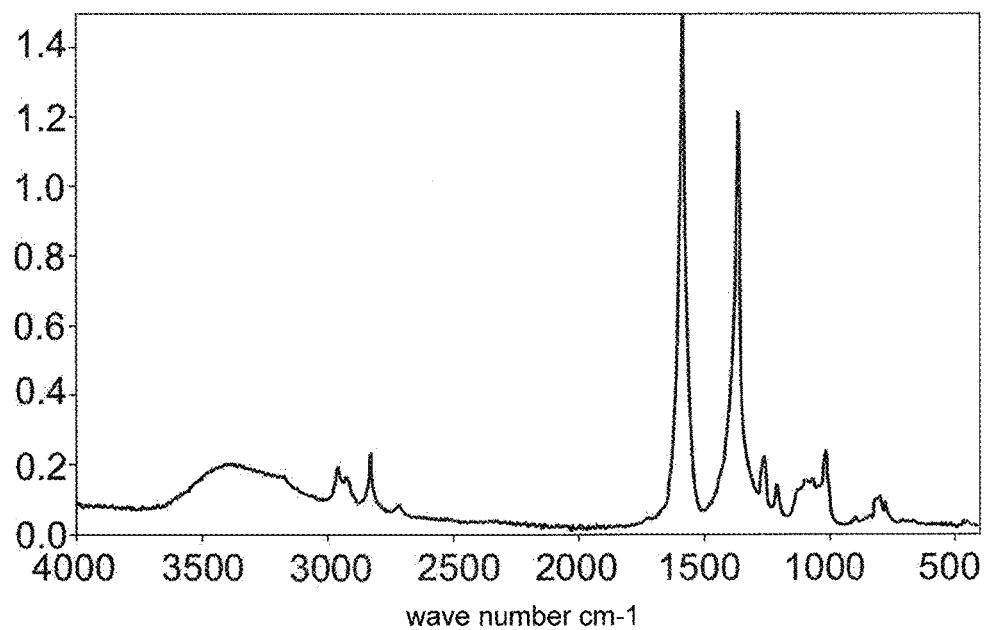
FIG. 5 shows the FTIR-ATR spectrum of a commercially available fiber article.
Figure 6:
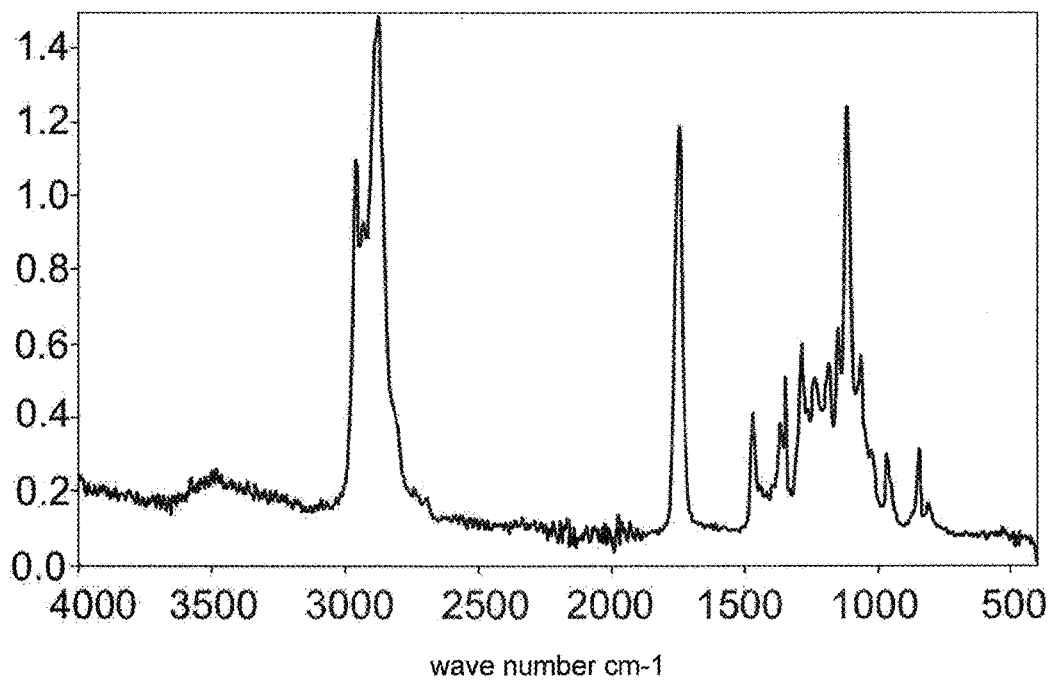
FIG. 6 shows the FTIR-ATR spectrum of a commercially available fiber article.

An IR spectrum was taken from a glass fiber bundle made of the optical fibers coated with the size solution. For that, the glass fiber bundle was pressed onto the ATR crystal of the measuring device several times. Here, little amounts of the size were transferred onto the crystal and then measured. The FTIR-ATR spectrum of sample E14 is shown in FIG. 2 and that of sample E18 is shown in FIG. 3.

Examples E23 and E24

A size solution, such as described for the examples E2 to E22, using water and ethanol, however without acetic acid, was prepared.

| | Example | |
|---|---|---|
| | E23 | E24 |
| Ami-Si | 8.93% | 5.6% |
| Alk-Si | 19.30% | 12.1% |
| PEG400 | 31.90% | 20.0% |
| stearic acid | 39.87% | 25.0% |
| glycerin | | 50.0% |
| pressing-out force | 1450 N | 1550 N* |
| failure | F-H | F-H |

For both size solutions, the press force was very good. In the case of E24, the excellent value was achieved at increased temperature.

Figure 7:
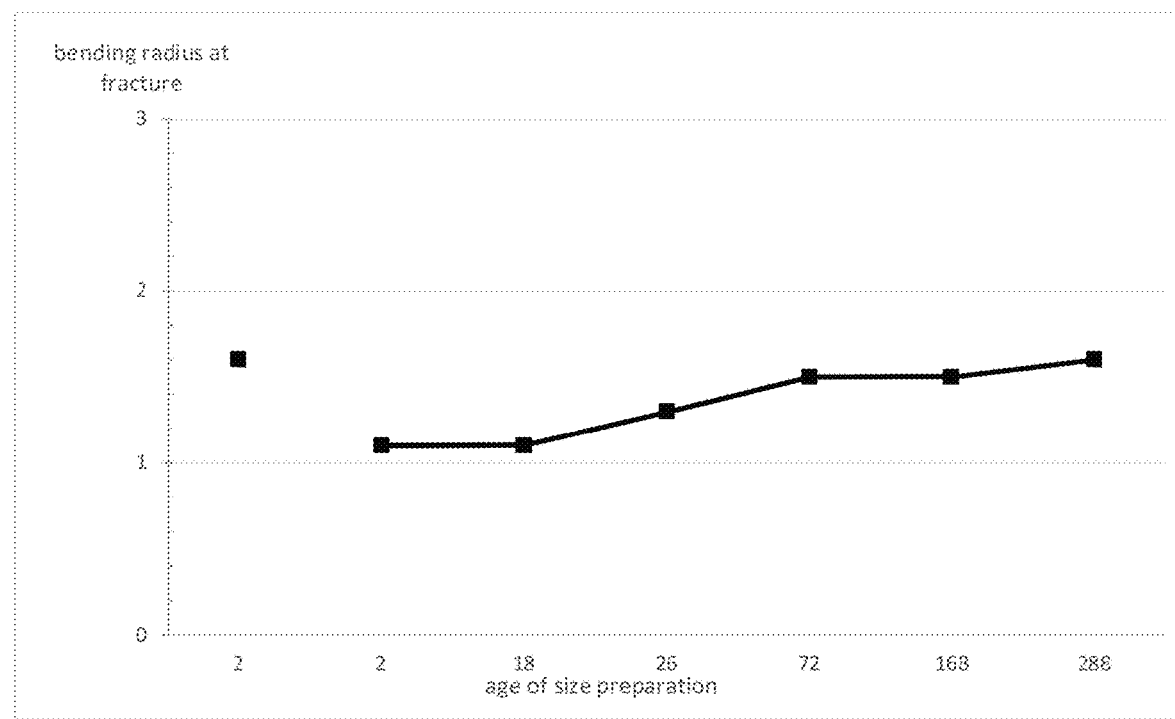
FIG. 7 shows the achieved bending radius in the breaking-loop test as a function of the idle time of the size solution in comparison to a size solution of prior art (single value).

It was examined, how the bending radius of a fiber coated with the size E23 changed as a function of the idle time of the blended size solution. The results are shown in FIG. 7. It can be seen that, at first, the bending radius is just above 1 mm and that it, with the idle time of the size solution, becomes slightly larger up to values in the range of about 1.6 mm. Only after 288 hours a bending radius is achieved which is comparable with prior art without functional silane (single measuring point).

Figure 8:
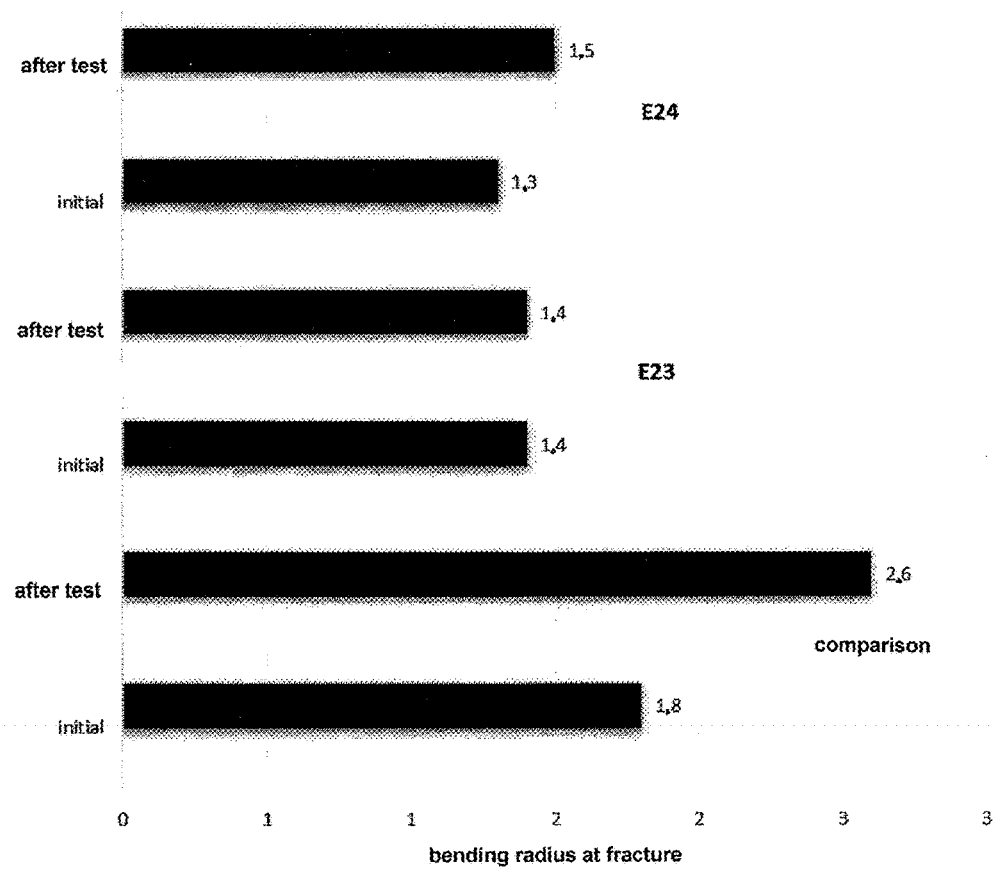
FIG. 8 shows the development of the bending radius of fibers according to the present invention in the breaking-loop test after frequent temperature changes.

FIG. 8 shows how the results of the breaking-loop test change after the fibers were subjected to frequent temperature changes. For that, the bundles were cooled and heated 50 times from −40° C. to +80° C. with a rate of 2 K/min at 0% air moisture. It was revealed that the fibers treated with E23 and E24 after the test showed the same very good result in the breaking-loop test like before the test. A comparative fiber coated with a size according to prior art—without functional silane—showed considerable impairment. Similarly good results were obtained in the case of storage for 400 hours at 85° C. and 85% air moisture as well as storage for 10 days in 90° C. hot water.

Figure 9:
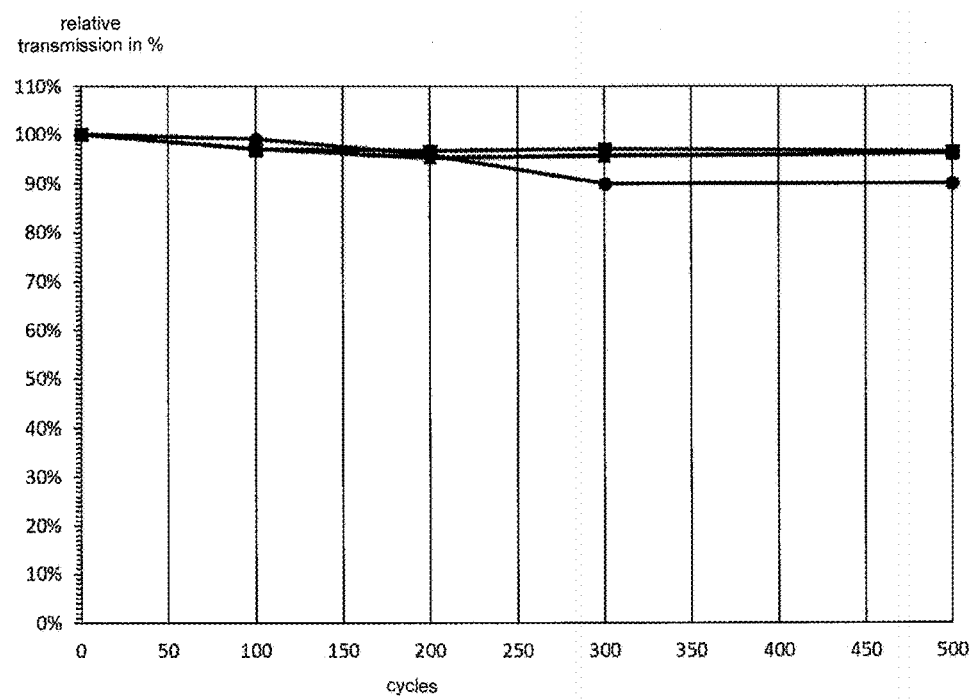
FIG. 9 shows the change of the optical transmission of fiber bundles according to the present invention after hundreds of purification and sterilization cycles.

The extent of the impairment of the transmission of fiber bundles coated with the size solution in the case of strong purification stress was examined. For that, the fiber bundles were subjected to 500 cycles of purification and subsequent thermal disinfection, wherein after 20 purification steps 50 sterilization steps each followed. FIG. 9 shows that the transmission of the fiber treated with the size according to the present disclosure (squares=E23; triangles=E24) only marginally deteriorated to about 97%, while the comparative bundles (circles; no functional silane) partially declined down to 90%. The data show an excellent chemical resistance and hydrolytic stability.

Figure 10:
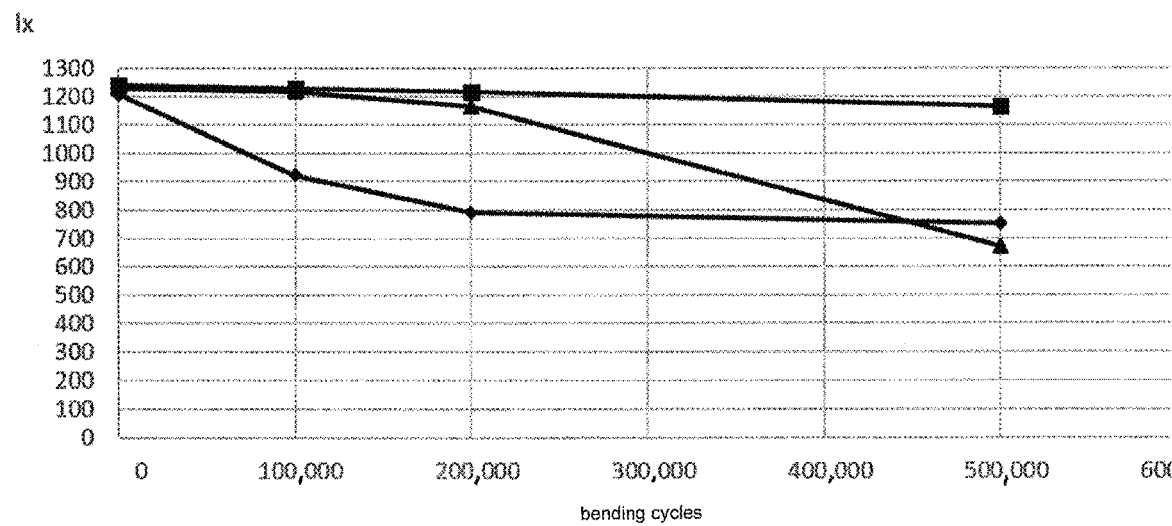
FIG. 10 shows the development of the achieved illuminance after repeated bending of fibers provided with a coating according to the present invention in comparison with prior art without functional silane.

FIG. 10 shows the development of the achieved illuminance after repeated bending to a bending radius of 2 mm with bending angles of −90° to +90°, a cycle time of 2 s and an axial load of 5 N according to IEC 60794-1-6/E6. It can be seen that the size solution E23 (squares) provides the best results. E24 (triangles) is better than prior art without functional silane (rhombi).

LIST OF REFERENCE SIGNS

1 fiber core
2 cladding
3 functional layer
4 siloxane bond between an alkylsilane of the functional layer and the surface of the cladding layer
5 hydrogen bond between a functional group of the surface of the cladding layer and a polyethylene glycol of the functional layer
6 alkylsilane
7 aminosilane
8 polyethylene glycol
9 fatty acid

What is claimed is:
1. An optical fiber article, comprising:
an optical fiber; and
a functional layer on the surface of the optical fiber,
wherein the functional layer comprises at least one functional silane having the following structural formula:

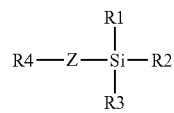

wherein Z is a branched or unbranched alkyl group or aryl group with 1 to 18 carbon atoms,
wherein R1, R2 and R3 are independently selected from hydrogen, oxygen, alkyl, alkyloxy, hydroxyalkyl and hydroxyl, and wherein one, two or three of the groups R1, R2 or R3 is connected to the surface of the optical fiber directly or indirectly via a covalent bond,
wherein R4 is selected from —NH$_2$, —NHR', —NR'R", glycidyloxy and —SH, wherein R' and R" are independently selected from alkyl, aminoalkyl, hydroxyalkyl and —(CH$_2$)$_m$NH$_2$, wherein m is 1 to 6, and
wherein the functional layer is a dry functional layer that comprises less than 35% by weight of a liquid component having a boiling point at 1013 hPa of higher than 100° C.

2. The optical fiber article according to claim 1, wherein the photopolymerized polymers are present in an amount that is less than 1% by weight, based on the weight of the functional layer.

3. The optical fiber article according to claim 1, wherein the polyacrylates, polymethacrylates, polyvinyl polymers, polystyrene and/or derivatives thereof in the functional layer are present in an amount that is less than 1% by weight, based on the weight of the functional layer.

4. The optical fiber article according to claim 1, wherein the optical fiber article comprises less than 500 ppm (m/m) of a halide.

5. The optical fiber article according to claim 1, wherein the functional layer comprises at least one fatty acid.

6. The optical fiber article according to claim 1, wherein the optical fiber has a bending radius of less than 10 mm when measured in the breaking-loop test according to DIN 58141-6:2011.

7. The optical fiber article according to claim 1, wherein the optical fiber article has a press force of at least 250 N.

8. The optical fiber article according to claim 1, wherein the optical fiber article is biocompatible according to at least one of ISO10993-1:2018, USP Class VI, and ISO10993-5:2009.

9. The optical fiber article according to claim 1, wherein the functional layer comprises at least one of an alkylsilane and a polyethylene glycol silane, covalently bound to the surface of the fiber.

10. The optical fiber article according to claim 1, wherein R4 is —NHR'; wherein R' is —(CH$_2$)$_m$NH$_2$, wherein m=2, and wherein Z is an unbranched alkyl group with 1 to 10 carbon atoms, preferably of 3 to 8 carbon atoms.

11. The optical fiber article according to claim 1, wherein the functional layer comprises a polyalkylene oxide.

12. The optical fiber article according to claim 1, wherein the optical fiber comprises a fiber core and a cladding and the functional layer is on a surface of the cladding.

13. The optical fiber article according to claim 1, wherein the optical fiber comprises a fiber core and/or cladding made of a multicomponent glass.

14. The optical fiber article according to claim 1, wherein the functional silane has formed a reaction product with one or more adhesives at least partially.

15. A light guide comprising the optical fiber article according to claim 1.

16. A method for the production of an optical fiber article according to claim 1, comprising the steps of:
a. providing at least one optical fiber;
b. coating at least a part of the optical fiber with a size; and
c. drying the size.

17. The method according to claim 16, further comprising the step of treating the dried size with a liquid component to obtain a wet size, wherein the liquid component has a boiling point at 1013 hPa of higher than 100° C.

18. The method according to claim 17, wherein the liquid component is selected from the group consisting of silicone oil, polyethylene glycol, alcohols, esters, ethers, ketones, acetates, and combinations thereof.

19. A method for the production of an optical fiber article, wherein the optical fiber article comprises:
an optical fiber; and
a functional layer on the surface of the optical fiber,
wherein the functional layer comprises at least one functional silane having the following structural formula:

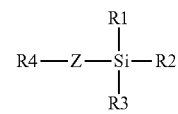

wherein Z is a branched or unbranched alkyl group or aryl group with 1 to 18 carbon atoms,
wherein R1, R2 and R3 are independently selected from hydrogen, oxygen, alkyl, alkyloxy, hydroxyalkyl and hydroxyl, and wherein one, two or three of the groups R1, R2 or R3 is connected to the surface of the optical fiber directly or indirectly via a covalent bond, and
wherein R4 is selected from —NH$_2$, —NHR', —NR'R", glycidyloxy and —SH, wherein R' and R" are independently selected from alkyl, aminoalkyl, hydroxyalkyl and —(CH$_2$)$_m$NH$_2$, wherein m is 1 to 6,
wherein the method comprises the steps of:
a. providing at least one optical fiber;
b. coating at least a part of the optical fiber with a size; and
c. drying the size; and
d. treating the dried size with a liquid component to obtain a wet size, wherein the liquid component has a boiling point at 1013 hPa of higher than 100° C.

20. The method according to claim 19, wherein the liquid component is selected from the group consisting of silicone oil, polyethylene glycol, alcohols, esters, ethers, ketones, acetates, and combinations thereof.

* * * * *